United States Patent
Nishio et al.

(10) Patent No.: US 7,222,516 B2
(45) Date of Patent: May 29, 2007

(54) GAS SENSOR, GAS SENSOR CAP, AND GAS SENSOR UNIT

(75) Inventors: Hisaharu Nishio, Nagoya (JP); Takashi Nakao, Nagoya (JP); Kazuhiro Kouzaki, Nagoya (JP)

(73) Assignee: NGK Spark Plug Co., Ltd., Aichi-ken (JP)

( * ) Notice: Subject to any disclaimer, the term of this patent is extended or adjusted under 35 U.S.C. 154(b) by 0 days.

(21) Appl. No.: 10/558,113

(22) PCT Filed: May 31, 2004

(86) PCT No.: PCT/JP2004/007479

§ 371 (c)(1),
(2), (4) Date: Nov. 23, 2005

(87) PCT Pub. No.: WO2005/012895

PCT Pub. Date: Feb. 10, 2005

(65) Prior Publication Data

US 2006/0243028 A1    Nov. 2, 2006

(30) Foreign Application Priority Data

May 29, 2003    (JP)    ............................. 2003-152275

(51) Int. Cl.
*G01N 7/00*    (2006.01)
(52) U.S. Cl. .................................... 73/23.31
(58) Field of Classification Search ............... 73/23.31, 73/23.32, 31.05, 31.06; 204/424, 425, 426, 204/427, 428, 429
See application file for complete search history.

(56) References Cited

U.S. PATENT DOCUMENTS

| 4,019,974 | A | * | 4/1977 | Weyl et al. ................. 204/428 |
| 4,116,797 | A | * | 9/1978 | Akatsuka .................... 204/428 |
| 4,588,494 | A | * | 5/1986 | Kato et al. .................. 204/426 |
| 4,786,397 | A | * | 11/1988 | Barbieri et al. ............. 204/427 |
| 5,098,548 | A | * | 3/1992 | Duce .......................... 204/424 |
| 5,139,639 | A | * | 8/1992 | Holleboom ................. 204/427 |

(Continued)

FOREIGN PATENT DOCUMENTS

JP    53-95884    8/1978

(Continued)

Primary Examiner—Michael Cygan
(74) Attorney, Agent, or Firm—Sughrue Mion, PLLC

(57) ABSTRACT

The invention presents a gas sensor low in cost and easy to form a terminal member, a gas sensor cap connected to the gas sensor for sending an output signal to an external device, and a gas sensor unit capable of holding a stable electrically connected state between the terminal member of the gas sensor and the gas sensor cap. The gas sensor 100 of the invention includes a gas detecting element 120 and a terminal member 150. The terminal member 150 is made of a plate material bent and processed into a predetermined shape, and includes a tubular output-side terminal portion 151 electrically connected to a cap terminal 211 for sending an output signal of the gas detecting element 120, which is the output-side terminal portion 151 expanding elastically in diameter when connected to the cap terminal 211, and a tubular element-side terminal portion 153 connected electrically to an inside electrode 112, which is the element-side terminal portion 153 inserted into the gas detecting element 120 while contracting elastically in diameter.

16 Claims, 10 Drawing Sheets

U.S. PATENT DOCUMENTS

| | | | |
|---|---|---|---|
| 5,490,412 A * | 2/1996 | Duce et al. | 73/23.31 |
| 5,759,365 A * | 6/1998 | Yamada et al. | 204/424 |
| 2002/0134678 A1 * | 9/2002 | Vargo et al. | 204/428 |
| 2004/0074284 A1 | 4/2004 | Day et al. | |

FOREIGN PATENT DOCUMENTS

| | | |
|---|---|---|
| JP | 53-95886 | 8/1978 |
| JP | 56-131451 U | 10/1981 |
| JP | 56-175752 U | 12/1981 |
| JP | 58-165577 A | 9/1983 |
| JP | 11-153570 A | 6/1999 |
| JP | 2002-296218 A | 10/2002 |

* cited by examiner

GAS SENSOR, GAS SENSOR CAP, AND GAS SENSOR UNIT

TECHNICAL FIELD

The present invention relates to a gas sensor having a ceramic gas detecting element, a gas sensor cap put on the gas sensor for transmitting the output from the gas sensor to outside, and a gas sensor unit combining them.

BACKGROUND ART

Hitherto, various devices have been proposed as gas sensors having ceramic gas detecting elements. These gas sensors have gas detecting elements made of zirconia ceramics of oxygen ion conductivity, for example, and are installed in exhaust pipes of an internal-combustion engine for detecting the oxygen concentration in the emission (see, for example, patent document 1 and patent document 2).

[Patent document 1] Unexamined utility model application publication No. S53 (1978)-95884

[Patent document 2] Unexamined utility model application publication No. S53 (1978)-95886

DISCLOSURE OF THE INVENTION

Problem to be Solved by the Invention

The gas sensors disclosed in patent document 1 and patent document 2 have ceramic gas detecting elements in a tubular form with a bottom, and tubular terminal members for sending output signals from the gas detecting elements to outside. The terminal members are formed by processing a bar metal element (bar material or pipe material), and is hence expensive. Further, the terminal member has a high rigidity, and an elastic conductive packing is interposed between the terminal member and the gas detecting element so as to improve the electric connection with the inside electrode formed on the inner surface of the gas detecting element. As a result, the gas sensors disclosed in patent document 1 and patent document 2 are much more expensive.

In patent document 1 and patent document 2, nothing is mentioned about a connecting cord for electrically connecting the gas sensor and an external device (for example, ECU), but there was a risk of causing noise due to momentary disconnection between terminal member of gas sensor and terminal of connecting cord by the influence of vibration or the like. Accordingly, there has been a desire for development of a gas sensor, an electric connection parts such as a connecting cord (a gas sensor cap) and a gas sensor unit comprising them, which are capable of holding a stable electric connection state between terminal member of gas sensor and external terminal (cap terminal) provided in connecting cord (gas sensor cap).

The invention is devised in the light of such present circumstances, and it is hence an object thereof to present a gas sensor with a terminal member to be formed easily at low cost, a gas sensor cap being connectable to the gas sensor for transmitting an output signal to outside device, and a gas sensor unit capable of holding stable electric connection state between the terminal member of gas sensor and gas sensor cap.

Means for Solving the Problem

The solving means is a gas sensor comprising: a gas detecting element, and a terminal member connected to an electrode formed on the gas detecting element, the terminal member being connectable to an external terminal for sending an output signal from the gas detecting element to outside, wherein the terminal member includes: an output-side terminal portion engageable and electrically connectable with the external terminal for sending the output signal, the output-side terminal portion having a plurality of contact points at which the output-side terminal portion elastically contacts with the external terminal to hold the external terminal in a direction orthogonal to a moving direction that moves at least either the external terminal or the output-side terminal portion relatively when the terminal member is connected with the external terminal, and an element-side terminal portion electrically connected to the electrode.

In the gas sensor of the present invention, the output-side terminal portion of the terminal member has a plurality of contact points elastically contacting with the external terminal in the direction orthogonal to the moving direction.

Therefore, when the external terminal and the output-side terminal portion of the terminal member are connected, the output-side terminal portion contacts with the external terminal at the plural contact points and also elastically presses the external terminal and is electrically connected thereto. That is, conduction between the gas sensor and the external terminal can be assured through the plural contact points, and each contact point is pressed elastically. It hence lowers the risk of causing noise or the like (risk of decline of gas detection accuracy) due to momentary disconnection between the external terminal and the output-side terminal portion by the effects of vibration or the like. Moreover, since the output-side terminal portion of the gas sensor is elastically connected to the external terminal in the orthogonal direction, it is easy to attach to or detach from the output-side terminal portion by moving the external terminal relatively in the moving direction.

Furthermore, it is the role of the output-side terminal portion to elastically contact with and hold the external terminal at the plural contact points in the orthogonal direction, and the shape of the output-side terminal portion can be selected so properly as to effectively have the plural contact points in accordance with the shape of the external terminal. The shape of the output-side terminal portion should be different depending on the shape (form) of the external terminal, but, for example, a plate material may be rolled into tubular shape with a substantially C-shaped section orthogonal to the axial direction. A plate material may also be rolled into a tube by overlapping in part. In these forms, the output-side terminal portion elastically winds around the outer surface of the external terminal from its outside, or elastically presses to the inner surface of the tubular external terminal from the inside in the radial direction and expands it, thereby connecting with the external terminal. Accordingly, the output-side terminal portion has the plurality of contact points in surface or line contact with the outer surface or the inner surface of the external terminal depending on the form of the external terminal. Or plural contact points may be formed by contacting with protrusions formed the outer surface or inner surface of the external terminal. In the output-side terminal portion of these forms, the moving direction is the direction along the axis of the output-side terminal portion, and the orthogonal direction is the radial direction of the output-side terminal portion.

In the output-side terminal portion formed by winding the plate material like a tube with a C-shaped section orthogonal to the axial direction or winding the plate material like a tube by overlapping in a part, further, one or plural protrusions may be formed so as to contact with the external terminal. The output-side terminal portion may be formed in circular, polygonal or other shape in the sectional form orthogonal to the axial direction.

Further, the portion enclosed by two slits extending in the direction along the axial direction formed at the side surface of the cylindrical or tubular main body may protrude in arcuate shape toward the radially outer or inner side, and slit protrusions elastically movable in the radial direction may be scattered and disposed in plural positions along the periphery of the tubular main body. Moreover, on the side surface of cylindrical or tubular main body, leading ends of tongue portions formed by a U-shaped slit may protrude, obliquely toward the radially outer or inner side, and the tongue-like protrusions movable elastically in the radial direction may be scattered and disposed in plural positions along the periphery of the cylindrical main body.

In the output-side terminal portion of the gas sensor mentioned above, the plural contact points may be disposed on a virtual cylinder passing them, and the plural contact points may be designed to move so as to expand or contract the diameter of the virtual cylinder in diameter when connected to the external terminal.

In the gas sensor of the invention, the plurality of contact points of the output-side terminal portion is disposed on a virtual cylinder passing them, and the contact points move so as to expand or contract a diameter of the virtual cylinder when the output-side terminal portion is connected to the external terminal.

Therefore, when the external terminal and the output-side terminal portion of the terminal member are connected, the output-side terminal portion contacts with the external terminal at plural contact points, and is electrically connected with the external terminal while elastically pressing the external terminal to the radially outer or inner side of the virtual cylinder. That is, the contact points conducting between the gas sensor and external terminal are elastically pressing from the radially outer or inner side. Hence, momentary disconnection between the external terminal and the output-side terminal portion by vibration and the like can be prevented, attaching to or detaching from the external terminal is easy. Furthermore, when the output-side terminal portion and the external terminal are connected, the output-side terminal portion and external terminal can be connected from any direction without depending on connection directions around the axis of the virtual cylinder and thereby be installed more easily.

The virtual cylinder is formed by axially extending a virtual circle of a specific diameter, and the plural contact points are disposed on this virtual cylinder. When the plural contact points are positioned on one virtual circle, these plural contact points are same in the positions in the axial direction on the virtual cylinder, and are disposed at different positions in the peripheral direction.

In the form of the output-side terminal portion having plural contact points elastically contacting with the external terminal, and disposed on the virtual cylinder, and moving the contact points so as to expand or contract the diameter of the virtual cylinder when connected to the external terminal, though variable with the shape (form) of the external terminal, same as mentioned above, for example, a plate material may be wound like a tube, and the section orthogonal to the axial direction may be formed in a C form, or a plate material may be wound like a tube by overlapping in part. When the output-side terminal portion of these forms is connected to the external terminal of solid bar or hollow tube with a cylindrical outer surface, the output-side terminal portion contacts with the external terminal as if winding around the cylindrical outer periphery of the external terminal. In this case, therefore, it is in surface or line contact with the outer periphery of the external terminal and multiple contact points are present. These contact points are disposed on the virtual cylinder coinciding with the outer periphery of the external terminal. On the other hand, when the output-side terminal portion of these forms is not connected to the external terminal but is in free state, the contact points (positions planned to be contact points) are disposed on a virtual cylinder of smaller diameter than mentioned above. That is, in these output-side terminal portions, when connected to the external terminal, the contact points move so as to expand the diameter of the virtual cylinder. Using similar output-side terminal portions, when connected to the external terminal having plural protrusions projecting toward the radially outer side on the outer periphery, the output-side terminal portions contact with the external terminal so as to wind around the outer periphery of the external terminal, but the plural portions abutting with the peaks of protrusions of the external terminal become the contact points, and the contact points are disposed on the virtual cylinder. In free state, on the other hand, these contact points are disposed on the virtual cylinder of smaller diameter. Also in this case, in these output-side terminal portions, when connected to the external terminal, the contact points move so as to expand the virtual cylinder. Further, the slit protrusions may be scattered and disposed at plural positions in the peripheral direction of the cylindrical main body, or the tongue-like protrusions may be scattered and disposed at plural positions in the peripheral direction of the cylindrical main body.

In the gas sensor as set forth in claim 1 or claim 2, the gas detecting element is composed of ceramics, having a tubular form with a bottom closed at a leading end side in an axial direction of the gas detecting element, the electrode is an inside electrode formed on an inner surface of the gas detecting element, the terminal member is made of a plate material bent and formed in a predetermined shape, the output-side terminal portion is tubular, and is elastically expanded or contracted in diameter when connected to the external terminal, and the element-side terminal portion is tubular, and inserted as being elastically contracted in diameter in the gas detecting element, the element-side terminal portion being electrically connected to the inside electrode.

The gas sensor of the invention has the tubular output-side terminal portion being elastically expanded or contracted in diameter when connected to the external terminal. Therefore, when the external terminal and output-side terminal portion are connected, the output-side terminal portion is electrically connected while pressing the external terminal to the radially outer or inner side. It hence lowers the risk of causing noise or the like (risk of decline of gas detection accuracy) due to momentary disconnection between the external terminal and the output-side terminal portion by the effects of vibration or the like. Moreover, since the output-side terminal portion of the gas sensor is connected to the external terminal by its own (plate material) elasticity, it is easy to detach from or attach to the external terminal.

It further comprises a tubular element-side terminal portion which is elastically contracted in diameter when inserted into the gas detecting element, and electrically connected to the inside electrode. In this gas detecting element, therefore, the element-side terminal portion is electrically connected to the inside electrode while pressing the inside electrode from the inside to the radially outer side. It hence lowers the risk of causing noise or the like due to momentary disconnection between the two by the effects of vibration or the like. Moreover, since the element-side terminal portion is elastically contracted, it can be connected directly to the inside electrode. Thus, as compared with the conventional case of using an elastic conductive packing, since the conductive packing is not needed, the number of parts is curtailed, and the cost is reduced.

The terminal member having such output-side terminal portion and element-side terminal portion is formed of a plate material bent and processed into a predetermined shape. Hence, the terminal member itself is easy to form and low in cost.

The terminal member of the invention may be formed by connecting plural members of bent and processed plate materials by a welding or other method, but preferably it should be formed by using a single metal plate, and processing the output-side terminal portion and element-side terminal portion into a tubular form respectively.

The tubular form of the output-side terminal portion and element-side terminal portion is obtained by, for example, forming the section orthogonal to the axial direction in a C-form. Or the plate material may be wound in a tubular form by overlapping in part. The sectional form orthogonal to the axial direction is not limited to the C-form, but may include circular or polygonal shape.

In the gas sensor, preferably, the inside of the gas detecting element and the outside of the gas sensor should communicate with each other through the inside of the output-side terminal portion and element-side terminal portion of the terminal member.

As mentioned herein, the terminal member of the invention is formed of a bent and processed plate member, and has tubular output-side terminal portion and element-side terminal portion. Through the inside (in the tube) of the output-side terminal portion and element-side terminal portion, the inside (in the tube) of the gas detecting element and the outside of the gas sensor communicate with each other. In other words, the terminal member composes a ventilation passage for introducing reference gas (outer air) into the inside of the gas detecting element. Hence, in the gas sensor of the invention, it is not needed to form ventilation passage specially for introducing reference gas (outer air) into the inside of the gas detecting element, and the terminal member does not require an extra process of forming ventilation passage (for example, piercing process), so that the cost is lowered.

In the gas sensor, preferably, the element-side terminal portion of the terminal member is positioned at the leading end side in the axial direction from the output-side terminal portion. By defining such configuration relation of the output-side terminal portion and element-side terminal portion, it is easy to form the terminal member, and the cost of the gas sensor is lowered. Moreover, since the ventilation passage formed by this terminal element is extended in the axial direction, it is easier to introduce the reference gas (outer air) into the inside of the gas detecting element.

In any one of the gas sensors mentioned above, the output-side terminal portion is elastically contracted in diameter when inserted in the external terminal and connected thereto, and the output-side terminal portion has a rear end portion inwardly bent and positioned at a rear end side in the axial direction.

The terminal member formed of a bent plate material tends to be lower in rigidity as compared with one formed by processing a bar metal element. Of the terminal members, in particular, the output-side terminal portion connecting to the external terminal is likely to be loaded by effects of external vibrations, and lowering of rigidity is not preferred. In the gas sensor of the invention, by contrast, the rear end portion of the output-side terminal portion is bent inside, and the rear end is tapered to be smaller in diameter toward the end. Hence, the output-side terminal portion can be elastically contracted, and the rigidity is enhanced.

Another solving means is the gas sensor as set forth in claim 1 or claim 2, in which the gas detecting element is composed of ceramics, having a tubular form with a bottom closed at a leading end side in an axial direction of the gas detecting element, the electrode is an inside electrode formed on an inner surface of the gas detecting element, the gas sensor further comprises a tubular enclosure made of insulating ceramics and surrounding the gas detecting element and the terminal member, the terminal member is made of a plate material bent and formed in a predetermined shape, the output-side terminal portion is tubular, and is elastically expanded in diameter when the external terminal is inserted in the output-side terminal portion for connection, thereby reducing a gap between an outer surface of the output-side terminal portion and an inner surface of the tubular enclosure than before insertion, and the element-side terminal portion is tubular, and inserted as being elastically contracted in diameter in the gas detecting element, the element-side terminal portion being electrically connected to the inside electrode.

The terminal member of the gas sensor of the invention has the output-side terminal portion being elastically expanded in diameter when the external terminal is inserted in and connected to the terminal member, thereby reducing the gap between the outer surface of the output-side terminal portion and the inner surface of the enclosure smaller than before insertion of the external terminal. Therefore, when the external terminal is connected to the gas sensor of the invention, the gap between the inner surface of the enclosure and the outer surface of the output-side terminal portion is smaller than before connecting. Accordingly, in the gas sensor of the invention, the output-side terminal portion surrounded by the enclosure hardly oscillates in the radial direction even when it receives effects of external vibrations during use. This makes it possible to suppress fatigue rupture (crack, breakage, etc.) at the position between the output-side terminal portion and element-side terminal portion of the terminal member due to effects of vibrations.

The terminal member of the gas sensor of the invention is also made of a plate material bent and processed into predetermined shape. Hence, the terminal member itself is easy to form and is low in cost.

In the gas sensor, the element-side terminal portion of the terminal member may also be positioned at the leading end side in the axial direction from the output-side terminal portion. By defining such configuration relation of the output-side terminal portion and the element-side terminal portion, it is easier to form the terminal element, and hence the gas sensor is inexpensive. Further, the ventilation passage formed by this terminal member is extended in the axial direction, and it is easier to introduce reference gas (outer air) into the inside of the gas detecting element.

In any gas sensor mentioned above, preferably, the terminal portion is made of a single plate material formed integrally.

The gas sensor of the invention uses a terminal member formed integrally from a single plate material. Such terminal member is easy to form, and is hence low in cost.

In any one of the gas sensors described above, preferably, the output-side terminal portion of the terminal member has a C-shape in section orthogonal to the axis of the output-side terminal portion.

The gas sensor of the invention has the output-side terminal portion having a C-shape in the section orthogonal to the axis. Such output-side terminal portion is easy to form, and is wide in deformation region, and hence an output-side terminal portion having elasticity of relatively large coefficient of elasticity is realized, so that the external terminal can be held firmly.

Another solving means is a gas sensor cap connectable to a gas sensor having a gas detecting element and a terminal member having an output-side terminal portion for sending an output signal from the gas detecting element to outside, for transmitting the output signal to an external device, the gas sensor cap comprising: a cap terminal engageable and electrically connectable with the output-side terminal portion, a cover made of insulating rubber and formed to cover the cap terminal, and a lead wire connected electrically to the cap terminal for transmitting the output signal to the external device, wherein the cap terminal has enough rigidity to move a plurality of contact points of the output-side terminal portion elastically contacting with the cap terminal so that a virtual cylinder passing the contact points is expanded or contracted in diameter when the cap terminal is connected to the output-side terminal portion.

The cap terminal of the gas sensor of the invention has enough rigidity to move the plurality of contact points of the output-side terminal portion elastically contacting with the cap terminal so that a virtual cylinder passing the contact points is expanded or contracted in diameter when the cap terminal is connected to the output-side terminal portion. Therefore, when the output-side terminal portion and the cap terminal are connected (engaged), the contact points of the output-side terminal portion are electrically connected to the cap terminal while elastically pressing the cap terminal to the radially outer or inner side.

It hence lowers the risk of causing noise or the like (risk of lowering the gas detection accuracy) by momentary disconnection between output-side terminal portion and cap terminal due to effects of vibrations.

Preferably, the cap terminal is engageable with the output-side terminal portion of the terminal member of the gas sensor, and when engaged with the output-side terminal portion, it should have enough rigidity to move the plural contact points of the output-side terminal portion so as to expand or contract the diameter of the virtual cylinder on which the contact points are disposed, and it may be formed, for example, in circular columnar or cylindrical form. Although the outside diameter is changed in the axial direction, a cap terminal in the form of a solid bar or hollow tube, which has a taper shape, a reverse taper shape, or a small diameter in the middle of the axial direction, may be also used. Or a cap terminal of bell shape closed at one end may be also used.

Another solving means is a gas sensor cap as set forth in claim 8, in which the output-side terminal portion of the terminal member in the gas sensor is tubular and capable of being elastically expanded or contracted in diameter, and the cap terminal is tubular, having enough rigidity for expanding or contracting, without deforming itself, the output-side terminal portion in diameter when the cap terminal is connected to the output-side terminal portion.

The gas sensor cap of the invention has a tubular cap terminal having enough rigidity for elastically expanding or contracting the diameter of the output-side terminal portion of the terminal member without deforming itself when connected to the gas sensor. Therefore, when the output-side terminal portion and the cap terminal are connected (engaged), the output-side terminal portion is electrically connected to the cap terminal while elastically pressing the cap terminal to the radially outer or inner side. It hence lowers the risk of causing noise or the like (risk of lowering the gas detection accuracy) by momentary disconnection between the output-side terminal portion and the cap terminal due to effects of vibrations or the like. Besides, since the cap terminal and the output-side terminal portion of the terminal member are designed to be connected by the elastic force of the output-side terminal portion, detaching or attaching property of cap terminal in the output-side terminal portion of the terminal member may be enhanced.

Another solving means is a gas sensor cap connectable to any one of the gas sensors mentioned above for transmitting the output signal to an external device, in which the external terminal is a tubular cap terminal engageable and electrically connectable with the output-side terminal portion, and includes: a cover made of insulating rubber and formed to cover the cap terminal, and a lead wire connected electrically to the cap terminal for transmitting the output signal to the external device, and the cap terminal has enough rigidity for moving the plurality of contact points of the output-side terminal portion for expanding or contracting the virtual cylinder in diameter when the cap terminal is connected to the output-side terminal portion.

The gas sensor cap of the invention also has enough rigidity for moving the plurality of contact points of the output-side terminal portion disposed on the virtual cylinder for expanding or contracting the diameter of the virtual cylinder when the cap terminal is connected to the output-side terminal portion of the connection terminal of the gas sensor. Therefore, when the output-side terminal portion and the cap terminal are connected (engaged), the output-side terminal portion is electrically connected to the cap terminal while elastically pressing the cap terminal to the radially outer or inner side.

It hence lowers the risk of causing noise or the like (risk of lowering the gas detection accuracy) by momentary disconnection between the output-side terminal portion and the cap terminal due to effects of vibrations or the like. Besides, since the cap terminal and the output-side terminal portion of the terminal member are designed to be connected by the elastic force of the output-side terminal portion, detaching or attaching property of cap terminal in the output-side terminal portion of the terminal member may be enhanced.

Another solving means is a gas sensor unit comprising a gas sensor including a gas detecting element and a terminal member that is connected to an electrode formed in the gas detecting element and also is connected to an external terminal for sending an output signal from the gas detecting element to outside, and a gas sensor cap having a cap terminal serving as the external terminal connected to the terminal member of the gas sensor for transmitting the output signal to an external device, wherein the terminal member includes: an output-side terminal portion engaged and connected electrically with the cap terminal to send the output signal, the output-side terminal portion having a plurality of contact points at which the output-side terminal portion is elastically connected with the cap terminal along a direction orthogonal to a moving direction for relatively moving either the cap terminal or the output-side terminal portion when connected to the cap terminal.

The gas sensor unit of the invention has a gas sensor and a gas sensor cap. The output-side terminal portion of the terminal member of the gas sensor has the plurality of contact points at which the output-side terminal portion is elastically connected with the cap terminal of the gas sensor cap along the orthogonal direction when connected (engaged) with the cap terminal.

Since the output-side terminal portion has such configuration, in the gas sensor unit of the invention, the plural contact points of the output-side terminal portion are electrically connected to the cap terminal while elastically pressing the same. It hence lowers the risk of causing noise or the like (risk of lowering the gas detection accuracy) by momentary disconnection between output-side terminal portion and cap terminal due to effects of vibrations or the like.

Besides, since the cap terminal and the output-side terminal portion of the terminal member are designed to be connected by the elastic force of the output-side terminal portion along the orthogonal direction, detaching or attaching property of cap terminal in the output-side terminal portion of the terminal member may be enhanced when attaching to or detaching from the output-side terminal portion by moving the cap terminal relatively in the moving direction, and thereby the gas sensor cap can be detached from or attached to the gas sensor smoothly.

In the gas sensor unit described above, preferably, the plurality of contact points of the output-side terminal portion of the terminal member is disposed on a virtual cylinder passing them, and the contact points move so as to expand or contract a diameter of the virtual cylinder when the output-side terminal portion is connected to the cap terminal.

In the gas sensor unit of the invention, the output-side terminal portion of the terminal member has the plurality of contact points elastically contacting with the cap terminal, being disposed on the virtual cylinder, and moves to expand or contract the diameter of the virtual cylinder passing these contact points when contacting with the cap terminal.

Since the output-side terminal portion has such configuration, in the gas sensor unit of the invention, the plural contact points of the output-side terminal portion are electrically connected to the cap terminal while elastically pressing the same to the radially outer side or radial inner side. Hence, momentary disconnection between the output-side terminal portion and the cap terminal due to vibrations or the like can be prevented, and the cap terminal can be detached from or attached to easily the output-side terminal portion of the terminal member, and moreover when connecting the output-side terminal portion to the cap terminal, there is no dependence on connection direction around the axis of the virtual cylinder, and the output-side terminal portion and the cap terminal can be connected from any direction, and it is further easier to install the gas sensor and gas sensor cap in this gas sensor unit.

In the gas sensor unit, preferably, the output-side terminal portion of the terminal member is tubular, and is elastically expanded or contracted in diameter when connected to the cap terminal, and the cap terminal is tubular, and is engaged with the output-side terminal portion by expanding or contracting the output-side terminal portion in diameter without deforming itself.

The gas sensor unit of the invention mentioned above comprises a gas sensor and a gas sensor cap. Specifically, the terminal member of the gas sensor has a tubular output-side terminal portion which is elastically expanded or contracted in diameter when connected to the cap terminal of the gas sensor cap. The gas sensor cap is engaged with the output-side terminal portion by expanding or contracting the diameter of the output-side terminal portion without deforming itself. Therefore, in the gas sensor unit of the invention, the output-side terminal portion is connected electrically to the cap terminal while elastically pressing the same in the radially outer or inner side. It hence lowers the risk of causing noise or the like (risk of lowering the gas detection accuracy) by momentary disconnection between the output-side terminal portion and the cap terminal due to effects of vibrations or the like.

Since the cap terminal and the output-side terminal portion of the terminal member are connected by the elastic force of the output-side terminal portion, it is easy to detach or attach the cap terminal from or to the output-side terminal portion of the terminal member, and hence the detaching and attaching property of gas sensor cap in the gas sensor can be enhanced.

In the gas sensor unit as set forth in claim 11 or claim 12, preferably, the gas sensor has a tubular enclosure made of insulating ceramics and surrounding the gas detecting element and the terminal member, the output-side terminal portion of the terminal member is tubular, and is elastically expanded in diameter when the cap terminal is inserted in of the output-side terminal portion, and the cap terminal has enough rigidity to expand the output-side terminal portion in diameter without deforming itself when inserted in and connected with the inside of the output-side terminal portion, and the cap terminal is inserted in and connected with an inside of the output-side terminal portion, the output-side terminal portion being elastically expanded in diameter, providing a smaller gap than before insertion between an outer surface of the output-side terminal portion and an inner surface of the tubular enclosure.

In the gas sensor unit of the invention, when the cap terminal is inserted in and connected to the output-side terminal portion, the output-side terminal portion is expanded elastically, and the gap between the outer surface of the output-side terminal portion and the inner surface of the enclosure becomes smaller than before insertion of the cap terminal. Hence, in the gas sensor unit of the invention, the output-side terminal portion surrounded by the enclosure hardly oscillates in the radial direction even when it receives effects of external vibrations. This makes it possible to suppress the fatigue rupture (crack, breakage, etc.) at the position between the output-side terminal portion and element-side terminal portion of the terminal member due to effects of vibrations.

In the gas sensor unit of the invention, since the cap terminal and the output-side terminal portion of the terminal member are connected by the elastic force of the output-side terminal portion, the cap terminal can be easily detached from or attached to the output side terminal of the terminal member, so that the detaching and attaching property of the gas sensor cap in the gas sensor is enhanced.

In any one of the gas sensor units described above, the gas detecting element is composed of ceramics, and has a tubular shape with a bottom closed at the leading end side in an axial direction of the gas detecting element, and the electrode is an inside electrode formed on the inner surface of the gas detecting element, and the terminal member is made of a plate material bent and formed in a predetermined shape and has a tubular element-side terminal portion inserted as being elastically contracted in diameter in the gas detecting element, the element-side terminal portion being electrically connected to the inside electrode.

The gas sensor unit of the invention has a tubular element-side terminal portion which is inserted in the tubular gas detecting element with a bottom while elastically contracting, and connected electrically to the inside electrode. Therefore, in the gas detecting element in this gas sensor unit, the element-side terminal portion is connected electrically to the inside electrode while pressing the inside electrode from the inside to the radially outer side. It hence lowers the risk of causing noise or the like due to momentary disconnection of the two due to effects of vibrations or the like. Moreover, since the element-side terminal portion is elastically contracted in diameter, it can be connected directly to the inside electrode. As compared with the conventional method of inserting an elastic conductive packing, this conductive packing is not needed, and the number of parts is curtailed and the cost is reduced.

The terminal member of the gas sensor unit of the invention is made of plate material bent and processed into predetermined shape. The terminal member is easy to form and is low in cost.

In the gas sensor unit, preferably, the gas sensor cap has an inside space communicating with outside, and inside of the gas detecting element and the inside space of the gas sensor cap are in communication with each other through inside of the output-side terminal portion and inside of the element-side terminal portion of the terminal member.

As described herein, the terminal member of the invention is made of a bent and processed plate material, and has a tubular output-side terminal portion and element-side terminal portion. Through the inside (in the tube) of the output-side terminal portion and element-side terminal portion, the inside (in the tube) of the gas detecting element and the inside space of the gas sensor cap communicate with each other. Further, the inside space of the gas sensor cap communicates with the outside. Therefore, in the gas sensor unit of the invention, the terminal member forms a ventilation passage for introducing outer air as reference gas into the inside of the gas detecting element by way of the inside space of the gas sensor cap. Hence, the gas sensor unit of the invention does not require particular ventilation passage for introducing the reference gas (outer air) into the inside of the gas detecting element, and the terminal member does not require the process (for example, piercing) of forming the ventilation passage, and hence the cost is lower.

In any one of the gas sensor units, the terminal member is made of a single plate material formed integrally.

The gas sensor unit of the invention uses a terminal member formed integrally from a single plate material. Such terminal member is easy to form, and is hence low in cost.

In any one of the gas sensor units described above, the output-side terminal portion of the terminal member of the gas sensor has a C-shape in section orthogonal to its axis.

In the gas sensor unit of the invention, the output-side terminal portion of the terminal member of the gas sensor has a C-shape in the section orthogonal to the axis. Such output-side terminal portion is easy to form, and is wide in deformation region, and hence an output-side terminal portion having elasticity of relatively large coefficient of elasticity is easily realized, so that the external terminal can be held firmly, and a reliable gas sensor unit is obtained.

In any gas sensor unit, preferably, the gas sensor has a tubular enclosure made of insulating ceramics and placed to surround the gas detecting element and terminal member, the gas sensor cap has a cover made of insulating rubber and formed to cover the cap terminal, and this cover includes an enclosure cover portion covering at least part of the tubular enclosure of the gas sensor connected with the gas sensor cap.

The gas sensor composing the gas sensor unit has an insulating ceramic enclosure surrounding the gas detecting element and terminal member. Hence, in a gas sensor unit having its enclosure exposed to outside, the ceramic enclosure may be broken when a foreign matter collides from outside.

By contrast, in the gas sensor unit of the invention, the cover of the gas sensor cap, made of insulating rubber, includes the enclosure cover portion covering at least part of the enclosure when the gas sensor cap and gas sensor are connected. Hence, if a foreign matter collides against the enclosure from outside, the portion of the enclosure covered with the rubber enclosure cover portion can be protected from breakage.

In the gas sensor unit, preferably, the enclosure cover portion of the gas sensor cap has an annular close-contact portion held circumferentially in close contact with an outer surface of the tubular enclosure, and the close-contact portion is in contact with an outer surface of a rear end portion of the tubular enclosure positioned at a rear end side in the axial direction thereof when the gas sensor cap is connected to the gas sensor.

In the gas sensor unit of the invention, the enclosure cover portion made of rubber has an annular close-contact portion capable of making contact with the outer surface of the enclosure along the peripheral direction (360 degrees) thereof. Hence, invasion of water into the gas sensor unit from the gap of the gas sensor and gas sensor cap can be prevented.

Incidentally, the gas sensor unit of the invention is, for example, installed in an exhaust pipe of an internal-combustion engine, and can be used for detecting the oxygen concentration in the emission. In this case, the gas detecting element is exposed to high temperature, and the gas detecting element and the metal casing surrounding the radial direction of the gas detecting element are heated to high temperature by the exhaust heat, and this heat is transmitted to the enclosure cover. By the effect of exhaust heat, the rubber enclosure cover portion (cover) may deteriorate.

By contrast, in the gas sensor unit of the invention, the close-contact portion of the enclosure cover portion contacts with the outer periphery at the rear end portion positioned at the rear end in the axial direction of the enclosure when the gas sensor cap and gas sensor are connected. Therefore, the close-contact portion covers and protects the enclosure, and contacts (closely contacts) with the enclosure at a position remote from the gas detecting element at high temperature. Hence, the gas sensor unit of the invention lowers the risk of deterioration of rubber enclosure cover portion (cover) due to effects of exhaust heat.

As the insulating rubber for composing the cover, a fluorine rubber is preferred. By using fluorine rubber, while having good heat-resistance, tight contact with the enclosure is assured.

EXPLANATION OF REFERENCE NUMERALS

Figure 1:
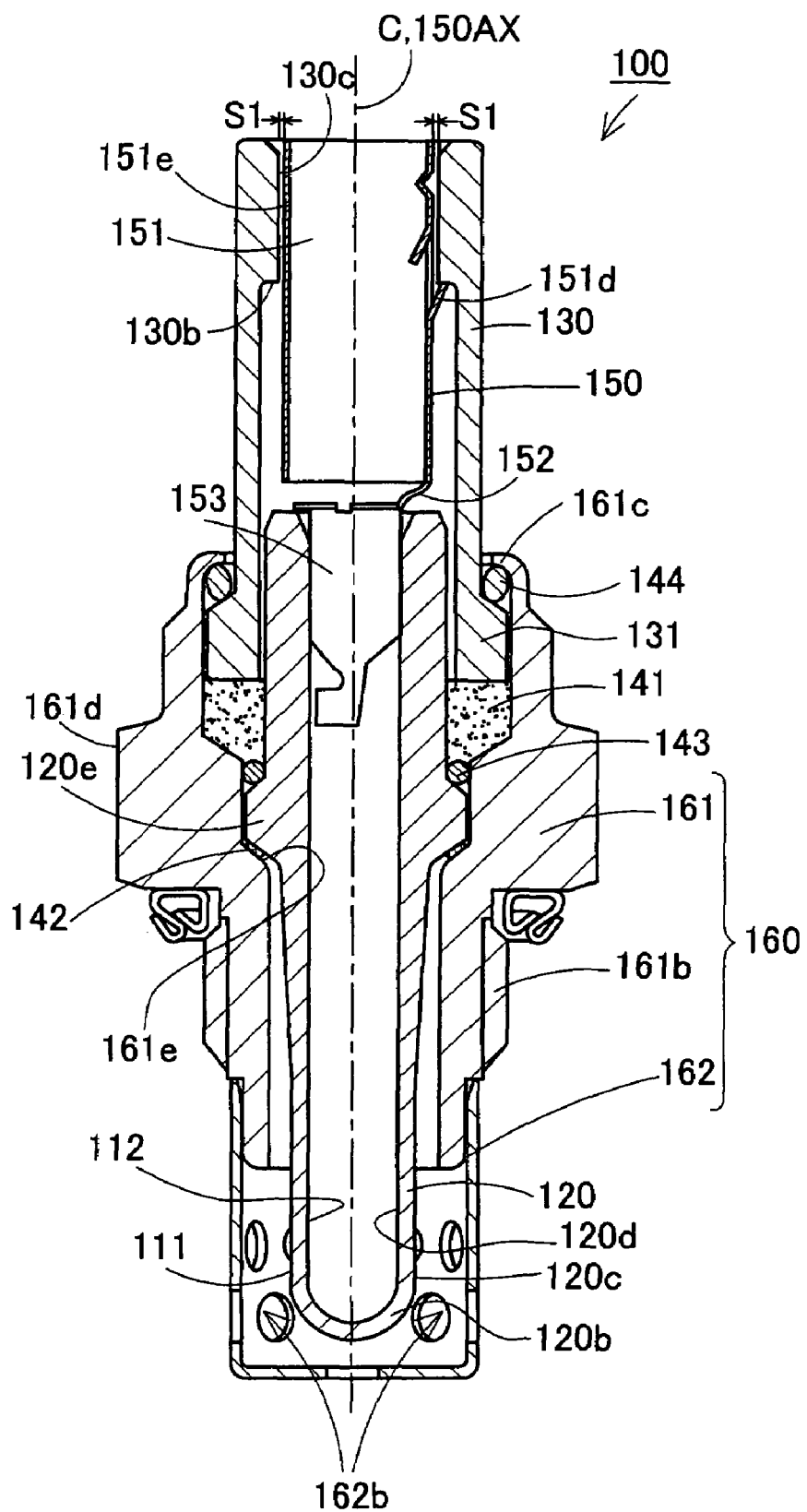
FIG. 1 is a partial sectional view of a gas sensor 100 in a first embodiment.

100, 400 Gas sensor
112 Inside electrode
120 Gas detecting element
130, 430 Enclosure
150, 450, 750, 850 Terminal member
151, 451, 751, 851 Output-side terminal portion
153, 453 Element-side terminal portion
200, 500 Gas sensor cap
210, 510 Cap terminal member
211, 511 Cap terminal (external terminal)
220, 520 Cover
221, 521 Enclosure cover portion
221*c*, 521*c* Close-contact portion
230 Lead wire
300, 600 Gas sensor unit

BEST MODE FOR CARRYING OUT THE INVENTION

Embodiment 1

A first embodiment of the invention is described below while referring to the accompanying drawings.

FIG. 1 is a partial sectional view of a gas sensor 100 in the first embodiment. The gas sensor 100 comprises a gas detecting element 120, an outside electrode 111, an inside electrode 112, an enclosure 130, a terminal member 150, and a casing 160.

The casing 160 has a main body fitting 161 and a protector 162. The main body fitting 161 is made of SUS430, and is formed in a cylindrical shape. The main body fitting 161 has an inner peripheral supporting portion 161*e* for supporting a flange portion 120*e* of the gas detecting element 120 described below, that is, the tapered inner peripheral supporter 161*e* expanding in diameter toward the rear end is disposed on the periphery to protrude from the inner surface toward the radial inner side. Outside of this main body fitting 161, a threaded portion 161*b* is formed for fixing the gas sensor 100 in an exhaust pipe 10 (see FIG. 4), and in the rear end side of the threaded portion 161*b* has a hexagonal portion 161*d* for engaging with a mounting tool for screwing the threaded portion 161*b* into the exhaust pipe is formed.

The protector 162 is a metal cylindrical tube, and has vent holes 162*b* for introducing the emission in the exhaust pipe 10 into the gas sensor 100.

The gas detecting element 120 is composed of a solid electrolyte having oxygen ion conductivity, and has a cylindrical shape extending in axis C direction, having a bottom and closed at the leading end 120*b*. The flange portion 120*e* protruding outward in the radial direction is provided on the outer surface of the gas detecting element 120, and a metal packing 142 is inserted between the leading end of the flange portion 120*e* and the inner peripheral supporter 162*e* of the main body fitting 161, and the gas detecting element 120 is disposed in the main body fitting 161. As the solid electrolyte composing the gas detecting element 120, a representative example is $ZrO_2$ with solid solution of $Y_2O_3$ or CaO, but a solid solution of $ZrO_2$ with other oxide such as alkaline earth metal or rare earth metal may be used. Further, $HfO_2$ may be contained.

In this embodiment, the leading end 120*b* side in the axis line C direction of the gas detecting element 120 is the leading end side, and the opposite side is the rear end side. This relation is the same in the other embodiments.

The outside electrode 111 is a porous material of Pt or Pt alloy, and is provided to cover the outer side 120*c* of the leading end 120*b* of the gas detecting element 120. The outside electrode 111 is disposed up to the leading end of the flange portion 120*e*, and is electrically connected to the main body fitting 161 by way of the packing 142. The inside electrode 112 is also a porous material of Pt or Pt alloy, and is provided to cover the inner surface 120*d* of the gas detecting element 120.

The enclosure 130 is made of insulating ceramics (specifically, alumina), and has a cylindrical shape. The leading end portion 131 of the enclosure 130 is supported between the gas detecting element 120 and main body fitting 161, together with ceramic powder 141 formed of talc, in a manner to surround the periphery of the rear end portion of the gas detecting element 120.

Figure 2:
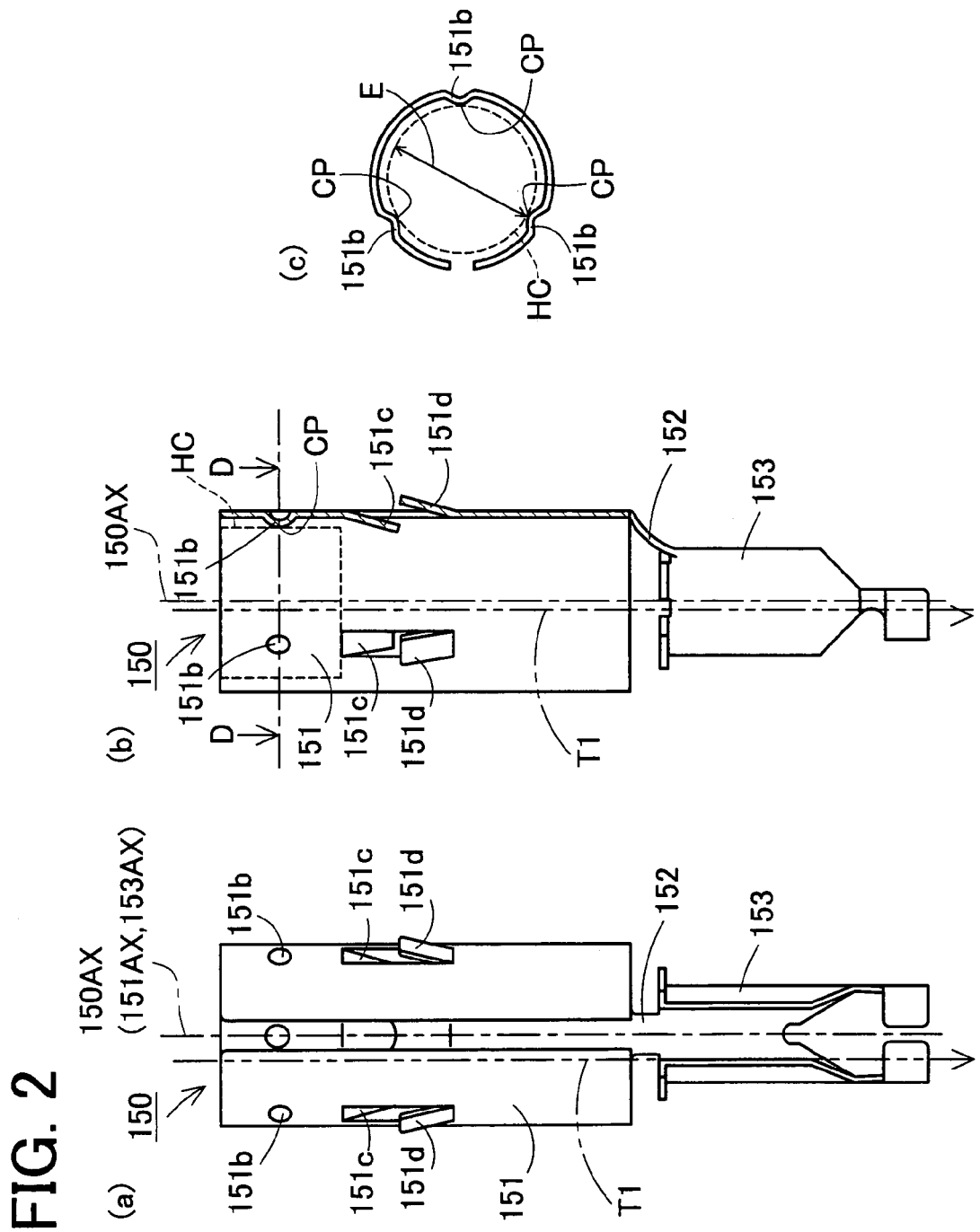
FIG. 2 is a diagram of a terminal member 150 in the first embodiment, in which (a) is a front view, (b) is a side view, and (c) is a sectional view taken in line D—D.

The terminal member 150 is made of, for example, SUS304, formed in a tubular shape as shown in FIG. 2, and has an output-side terminal portion 151, an element-side terminal portion 153, and a joint portion 152 for coupling them.

The output-side terminal portion 151 has a tubular form in C-shaped section (see FIG. 2 (c)) orthogonal to its axis line 151AX (axis line 150AX of terminal member), and is designed to expand elastically when a cap terminal 211 (see FIG. 3) of a cap terminal member 210 is relatively moved in the direction along the axis line 150AX (in the vertical direction in FIG. 1), and inserted and connected into the inside. Further, at three positions in the peripheral direction of the rear end side (above in the diagram) of the output-side terminal portion 151, bumps 151*b* protruding in the radial inner side are formed. As shown in FIG. 2(*c*), the inside peaks of these three bumps 151*b* are contact points CP elastically abutting against the cap terminal 211 along its radial direction. Diameter E of a virtual circle and virtual cylinder HC (broken lines in FIG. 2(*b*), (*c*)) making contact with the contact points CP of the three bumps 151*b* is the inside diameter of the output-side terminal portion 151.

Of the output-side terminal portion 151, three peripheral positions corresponding to the bumps 151*b* have an inside bent portions 151*c* folded at the radial inner side by blanking the wall surface, and outside bent portions 151*d* folded at the radially outer side. The inside bent portion 151*c* is formed to deflect elastically to the radially outer side when connected by inserting the cap terminal 211 (see FIG. 3) of the cap terminal 210 into the inside of the output-side terminal portion 151. The outside bent portion 151d, as shown in FIG. 1, abuts against the leading end surface of a shoulder 130b of the enclosure 130 when the terminal member 150 is assembled in the gas sensor 100, and prevents the output-side terminal portion 151 (terminal member 150) from slipping out.

The element-side terminal portion 153 has a tubular form of C-shaped section orthogonal to the axis line 153AX (axis line 150AX of terminal member). This element-side terminal portion 153 is inserted into the gas detecting element 120 while elastically contracting as shown in FIG. 1, and is connected electrically to the inside electrode 112. Therefore, in the gas sensor 100, the element-side terminal portion 153 is connected electrically while pressing the inside electrode 112 from the inside to the radially outer side. That is, the element-side terminal portion 153 elastically contacts with the inside electrode 112 at multiple contact points on its surface. Even if vibration is applied to the gas sensor 100, any one of the multiple contact points of the element-side terminal portion 153 is in contact with the inside electrode 112. It hence lowers the risk of causing noise or the like due to momentary disconnection of the two by the effects of vibrations or the like.

Besides, since the element-side terminal portion 153 contracts elastically, the element-side terminal portion 153 and the inside electrode 112 can be connected directly. Hence, as compared with the prior art of inserting an elastic conductive packing, since this conductive packing is not needed, the number of parts is curtailed and the cost is lowered.

Such terminal member 150 can be integrally formed by pressing, by using a single metal plate of predetermined shape. Forming of the terminal member 150 is hence easy and low in cost. Further, a metal plate is bent and processed to form such terminal member 150, and the output-side terminal portion 151 and the element-side terminal portion 153 positioned at the leading end side in the axis line 150AX direction (downward in FIG. 2) are formed in a tubular shape, and a ventilation passage T1 for introducing the reference gas (outer air) into the inside of the gas detecting element 120 is formed (see FIG. 2, FIG. 4). Hence, it does not require the process of forming the ventilation passage (for example, piercing process) after bending the terminal member 150, and hence the cost is lower.

Such gas sensor 100 is manufactured in the following procedure.

First, as shown in FIG. 1, a casing 160 is prepared by integrally forming a main body fitting 161 and a protector 162. Then, a gas detecting element 120 having an outside electrode 111 and an inside electrode 112 is inserted into the casing 160 together with a packing 142. Thereafter, a ring packing 143 is disposed at the rear end side of a flange portion 120e of the gas detecting element 120, the gap portion of main body fitting 161 and gas detecting element 120 is filled with a predetermined amount of ceramic powder 141. Then, a leading end portion 131 of an enclosure 130 is inserted between the gas detecting element 120 and the main body fitting 161 until coming into contact with the ceramic powder 141. After that, pressure is applied toward the leading end side of the enclosure 130, and under this pressure, a tightening ring 144 is inserted between a tightening portion 161c of main body fitting 161 and enclosure 130, and by tightening the tightening portion 161c, the constituent components are integrally fixed.

Finally, the terminal member 150 is inserted into the enclosure 130 and the gas detecting element 120. More specifically, the element-side terminal portion 153 is inserted into the gas detecting element 120 while contracting elastically, and is connected electrically to the inside electrode 112. At the same time, the output-side terminal portion 151 is disposed at the inside of the enclosure 130, and the outside bent portion 151d is fitted to the leading end of the shoulder 130b of the enclosure 130, so that the terminal member 150 is prevented from slipping out. A gap S1 is provided between the inner surface 130e of the enclosure 130 and the outer surface 151e of the output-side terminal portion 151.

Thus, the gas sensor 100 is completed.

Figure 3:
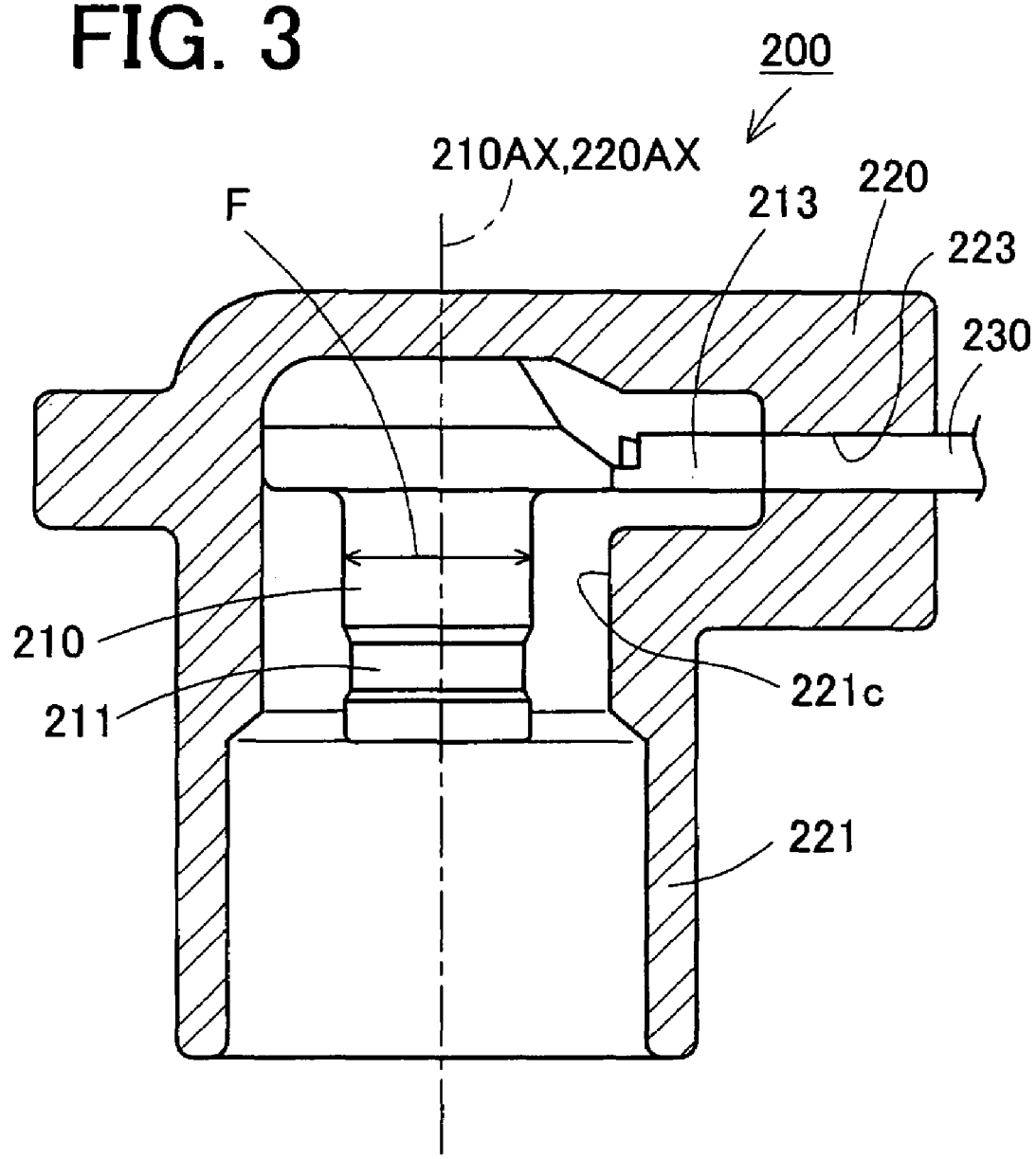
FIG. 3 is a partial sectional view of a gas sensor cap 200 in the first embodiment.

Next, the gas sensor cap 200 in the first embodiment is explained by referring to the drawing. FIG. 3 is a partial sectional view of the gas sensor cap 200. The gas sensor cap 200 comprises a cap terminal member 210, a cover 220 for covering the cap terminal member 210, and a lead wire 230.

The cap terminal member 210 is made of, for example, Inconel 718 (a trademark of Inconel of United Kingdom), and has a tubular cap terminal 211, and a tightening portion 213 for tightening and connecting the lead wire 230. The cap terminal 211 has enough rigidity for expanding the output-side terminal portion 151 in diameter without deforming itself when inserted and connected into the output-side terminal portion 151 of the gas sensor 100. The outside diameter of the cap terminal 211 is F.

The lead wire 230 has its one end tightened to the tightening portion 213 of the cap terminal member 210, and is electrically connected to the cap terminal 211. Through this lead wire 230, the output signal from the gas detecting element 120 of the gas sensor 100 can be transmitted to an external device (for example, engine control unit (ECU)).

The cover 220 is a hollow form made of fluorine rubber, having a cylindrical enclosure cover portion 221. The rear end side of the enclosure cover portion 221 is smaller in inside diameter as compared with the leading end side, and this portion is an contact portion 221c.

The gas sensor cap 200 is disposed in the cover 220 coaxially between the axis line 210AX of the cap terminal member 210 and the axis line 220AX of the enclosure cover portion 221, and the lead wire 230 connected to the cap terminal member 210 is extended outside from the insertion port 223.

Figure 4:
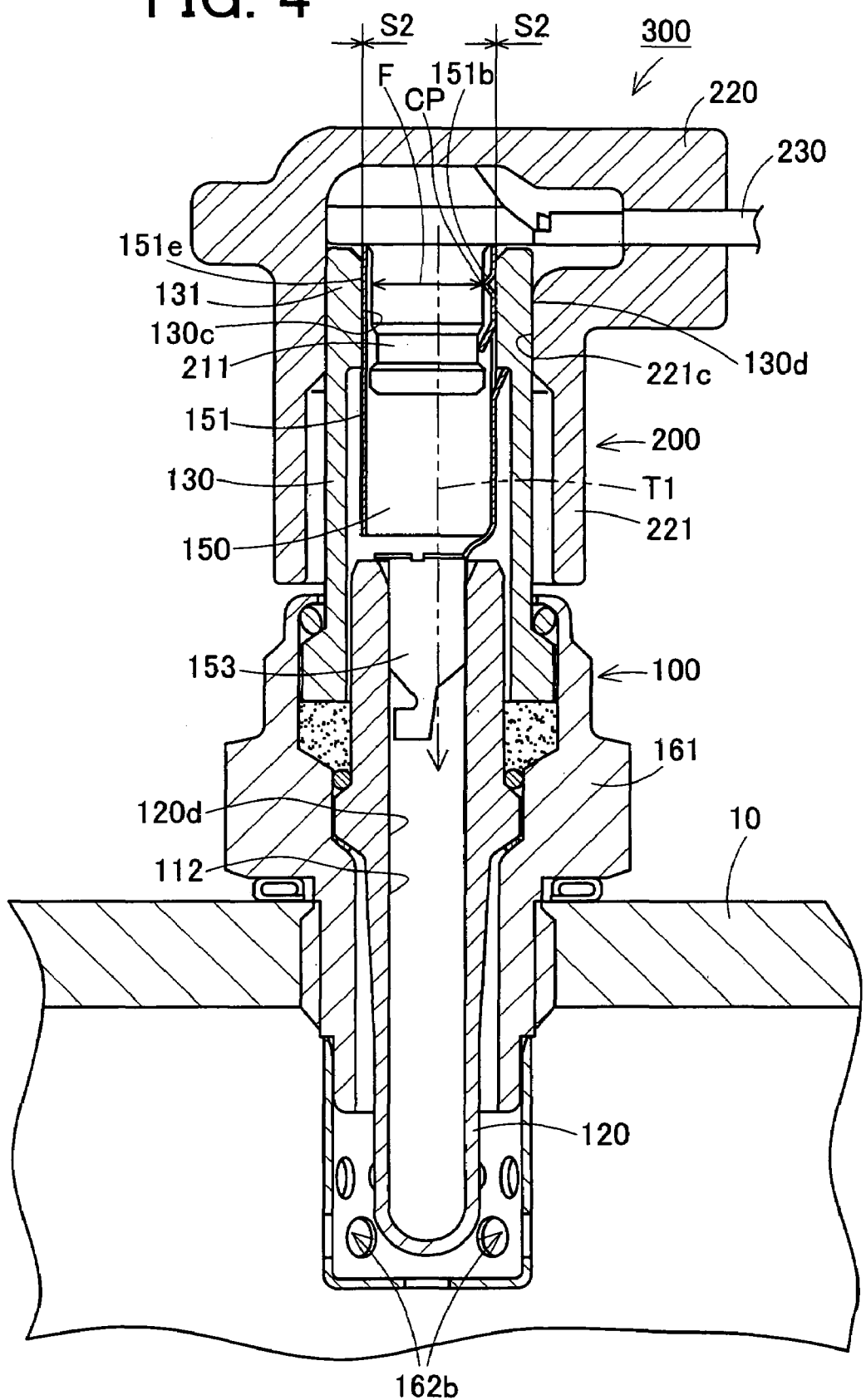
FIG. 4 is an explanatory diagram of a gas sensor unit 300 in the first embodiment, showing a mode of its use.

FIG. 4 shows a mode of use of the gas sensor unit 300 composed of gas sensor 100 and gas sensor cap 200 in the first embodiment. This gas sensor unit 300 can be used, for example, in detection of oxygen concentration in the emission of an internal-combustion engine.

More specifically, the gas sensor 100 is installed in the exhaust pipe 10, with the leading end side including the protector 162 positioned in the exhaust pipe 10, and the rear end portion from the threaded portion 161b of the main body fitting 161 exposed outside. At this time, the outside electrode 111 electrically connected to the main body fitting 161 is grounded through the main body fitting 161. Then, the cap terminal 211 of the gas sensor cap 200 is moved in the direction along its axis line 210AX (vertical direction in FIG. 3), and is inserted into the output-side terminal portion 151 of the gas sensor 100, so that the gas sensor cap 200 is fitted on the gas sensor 100.

At this time, since the inside diameter E (see FIG. 2) of the output-side terminal portion 151 is smaller than the outside diameter F of the cap terminal 211 (F<E), the output-side terminal portion 151 receives a force in the radially outer side from the cap terminal 211 at the bump 151b (contact point CP), and the output-side terminal portion 151 expands elastically in diameter.

Therefore, the output-side terminal portion 151 is connected electrically while elastically pressing the cap terminal 211 to the radial inner side, right after the plural (three in the embodiment) contact points CP. Thus, in the embodiment, the output-side terminal portion contacts with the cap terminal 211 at plural contact points CP. Since the contact points CP elastically press the cap terminal 211, it lowers the risk of causing noise or the like (the risk of lowering the gas detection accuracy) due to momentary disconnection between the output-side terminal portion 151 and cap terminal 211 by the effects of vibration of vehicle or the like. Since the gas sensor unit 300 is low in the risk of reduction of gas detection precision due to vibration effects, it can be favorably used in a two-wheel vehicle, in particular.

Further, by expansion of the diameter of the output-side terminal portion 151, the gap S2 between the outer surface 151e of the output-side terminal portion 151 and the inner surface 130c of the enclosure 130 is smaller than the gap S1 before inserting (S2<S1). Specifically, the gap S2 is almost zero, and the output-side terminal portion 151 contacts with the inner surface 130c of the enclosure 130. Accordingly, the output-side terminal portion 151 surrounded by the enclosure 130 hardly trembles in the radial direction due to effects of vibration of vehicle or the like, and fatigue rupture (crack, breakage, etc.) of the joint portion 152 of the terminal member 150 due to vibration effects can be suppressed. More specifically, in order that the output-side terminal portion 151 may be pressed tightly to the inner surface 130c of the enclosure 130, the dimensional relation is properly selected among the inside diameter E of the output-side terminal portion, the outside diameter of the cap terminal 211, and the inside diameter of the enclosure 130. Hence, the cap terminal 211 and the enclosure 130 are firmly integrated by way of the output-side terminal portion 151 of the terminal member 150, so that the gas sensor cap 200 is firmly held in the gas sensor 100.

On the other hand, the output-side terminal portion 151 is elastically connected to the cap terminal 211 along the radial direction (lateral direction in FIG. 4) orthogonal to the axis line 151AX (see FIG. 2), and by moving the cap terminal 211 in the direction (vertical direction in FIG. 3) along the axis line 210AX of the cap terminal member 210, it can be easily detached from or attached to the output-side terminal portion 151, and the detaching and attaching property is improved.

Moreover, the output-side terminal portion 151 and cap terminal 211 contact with each other at contact points CP disposed on the virtual cylinder HC, and when connecting the output-side terminal portion 151 and cap terminal 211, it is enough by inserting the cap terminal 211 into the output-side terminal portion 151, with the axis line 151AX (axis line C of gas sensor, see FIG. 2) of the output-side terminal portion 151 being coaxial with the axis line 210AX (see FIG. 3) of the cap terminal member 210. That is, to the output-side terminal portion 151 of the gas sensor 100 (see FIG. 4) installed in the exhaust pipe 10, the cap terminal 211 of the gas sensor cap 200 can be connected from any direction around its axis line C.

By fitting the gas sensor cap 200 to the gas sensor 100, the enclosure 130 can be covered by the enclosure cover portion 221 of the gas sensor cap 200. Hence, even if pebbles or foreign matters are thrown toward the enclosure 130 while the vehicle is running, the portion of the enclosure covered with the rubber enclosure cover portion 221 is protected from breakage. Especially, in the first embodiment, since the enclosure 130 is almost completely covered, the risk of direct collision of foreign matter against the enclosure 130 is low, and breakage of the enclosure 130 can be prevented.

Further, the annular contact portion 221c of the rubber enclosure cover portion 221 can be made contact tightly with the outer surface 130d of the enclosure 130 along the peripheral direction (360 degrees) thereof. Hence, invasion of water into the gas sensor unit 130 from the gap of the gas sensor 100 and gas sensor cap 200 can be prevented.

As shown in FIG. 4, the leading end of the gas sensor 100 is exposed to high temperature exhaust, and the gas detecting element 120 and the main body fitting 161 are heated to high temperature by the exhaust heat, and this exhaust heat is transmitted to the cover 220 of the gas sensor cap 200. By the effect of exhaust heat, the rubber enclosure cover portion 221 (cover 220) may deteriorate.

By contrast, in the gas sensor unit 300, the contact portion 221c of the enclosure cover portion 221 contacts with the rear end 131 positioned at the rear end of the enclosure 130. Therefore, the contact portion 221c covers and protects the enclosure 130, and contacts (closely contacts) with the enclosure 130 at a position remote from the leading end side (gas detecting element 120, etc.) of the gas sensor 100 at high temperature. Hence, it lowers the risk of deterioration of rubber enclosure cover portion 221 (cover 220) due to effects of exhaust heat.

In the gas sensor unit 300, the cover 220 is formed of fluorine rubber, and the heat resistance of the cover 220 is improved, and the contact to the enclosure 130 is also enhanced.

The lead wire 230 has multiple conductive wires, and through gaps among conductive wires, ventilation is possible in the lengthwise direction. In such gas sensor unit 300, reference gas (outer air) is introduced into the cover 220 from outside through the lead wire 230 of the gas sensor cap 200, and the reference gas can be taken into the inside (in the tube) of the gas detecting element 120 by way of the terminal member 150 (ventilation passage T1).

MODIFIED EXAMPLE

Figure 5:
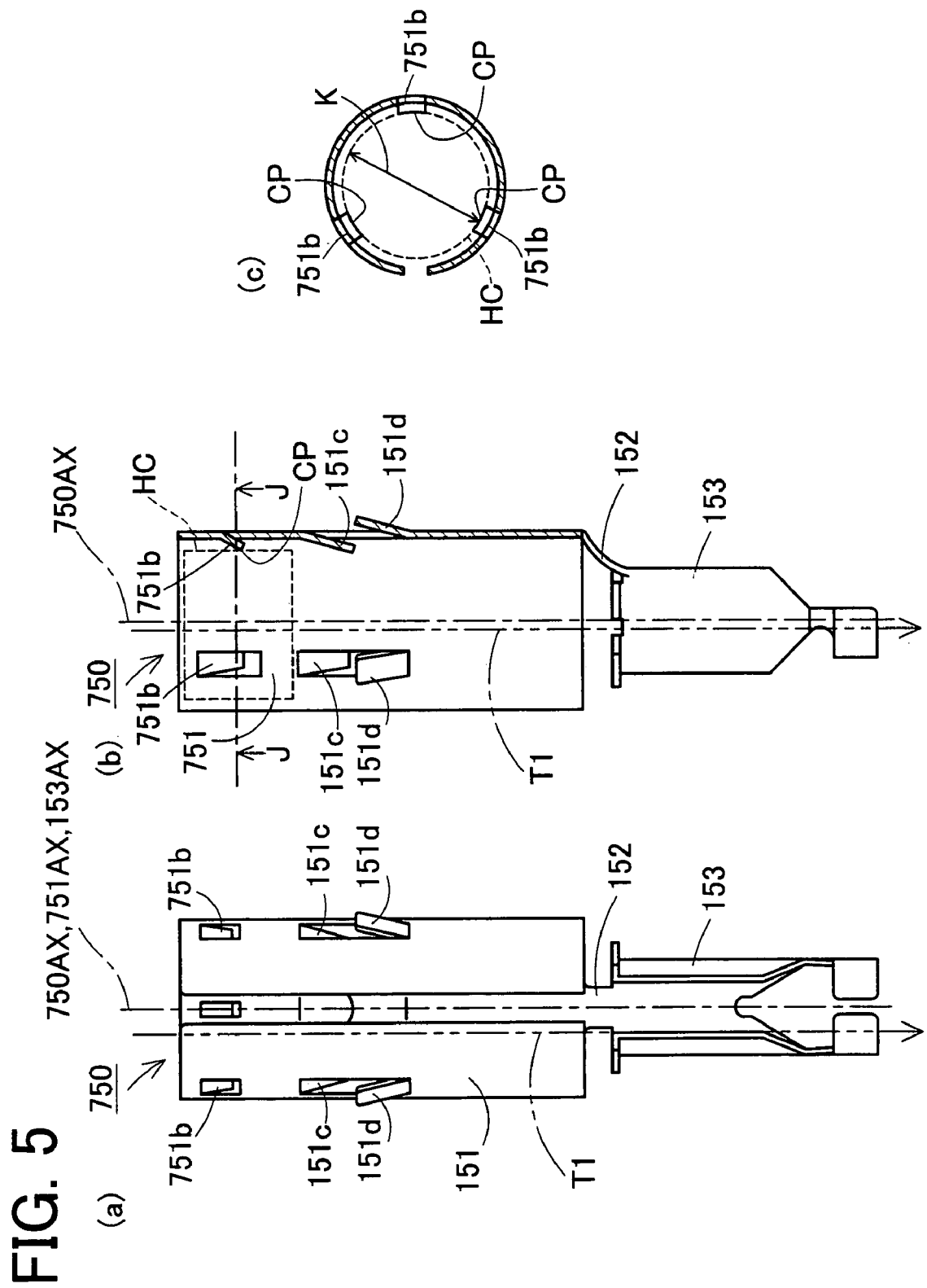
FIG. 5 is a diagram of a terminal member 750 in a modified example, in which (a) is a front view, (b) is a side view, and (c) is a sectional view taken in line J—J.

A modified example of the first embodiment is explained by referring to FIG. 5. This modified example is same in the parts of the gas sensor, gas sensor cap, and gas sensor unit, as shown in FIG. 5, except for a terminal member 750 which is different in shape from the terminal member 150 in the first embodiment. Therefore, only the shape of the terminal member 750 is explained.

The terminal member 750 (see FIG. 5) of the gas sensor in the modified example may be easily understood by comparison with the terminal member 150 (see FIG. 2) used in the gas sensor of the embodiment, and its element-side terminal portion 153 and joint portion 152 are same in the terminal member 150. On the other hand, its output-side terminal portion 751 is different from the output-side terminal portion 151 only in the point that an inside bent tongue portion 751b is formed instead of the bump 151b in the output-side terminal portion 151. That is, the output-side terminal portion 751 of the terminal member 750 has the inside bent tongue portions 751b, instead of the bumps 151b, at three positions in the peripheral direction.

The inside bent tongue portion 751b is a tongue-shaped portion formed by a U-slit provided in the output-side terminal portion 751, like the inside bent portion 151c, and its leading end protrudes obliquely to the radial inner side of the output-side terminal portion, and can be moved elastically in the radial direction. In this output-side terminal portion 751, therefore, the leading ends of the three inside bent tongue portions 751b are contact points CP contacting with the cap terminal 211, instead of the bumps 151b in the first embodiment, as shown in FIG. 5(c). In this modified example, diameter K of a virtual cylinder HC (indicated by a broken line in FIG. 5(b), (c)) contacting with the contact points CP of the three inside bent tongue portions 751b is supposed to be the inside diameter of the output-side terminal portion 751.

The output-side terminal portion 751 is a tubular form with a C-shaped section (see FIG. 5(c)) orthogonal to the axis line 751AX (axis line 750AX of terminal member), when the cap terminal 211 (see FIG. 3) of the cap terminal member 210 is inserted in and connected to the output-side terminal portion 751, the three inside bent tongue portions 751b are elastically moved to the radially outer side, and the inside diameter K is expanded elastically.

Therefore, also in the output-side terminal portion 751, too, the cap terminal 211 is connected electrically while elastically pressing to the radial inner side by the plural (three in this modified example) contact points CP. Thus, the output-side terminal portion 751 of the modified example contacts with the cap terminal 211 at plural contact points CP. Since the contact points CP are elastically pressing the cap terminal 211, it lowers the risk of causing noise or the like (risk of decline of gas detection accuracy) due to momentary disconnection between the output-side terminal portion 751 and the cap terminal 211 by the effects of vehicle vibration or the like.

Embodiment 2

A second embodiment of the invention is described below while referring to the accompanying drawings.

Figure 6:
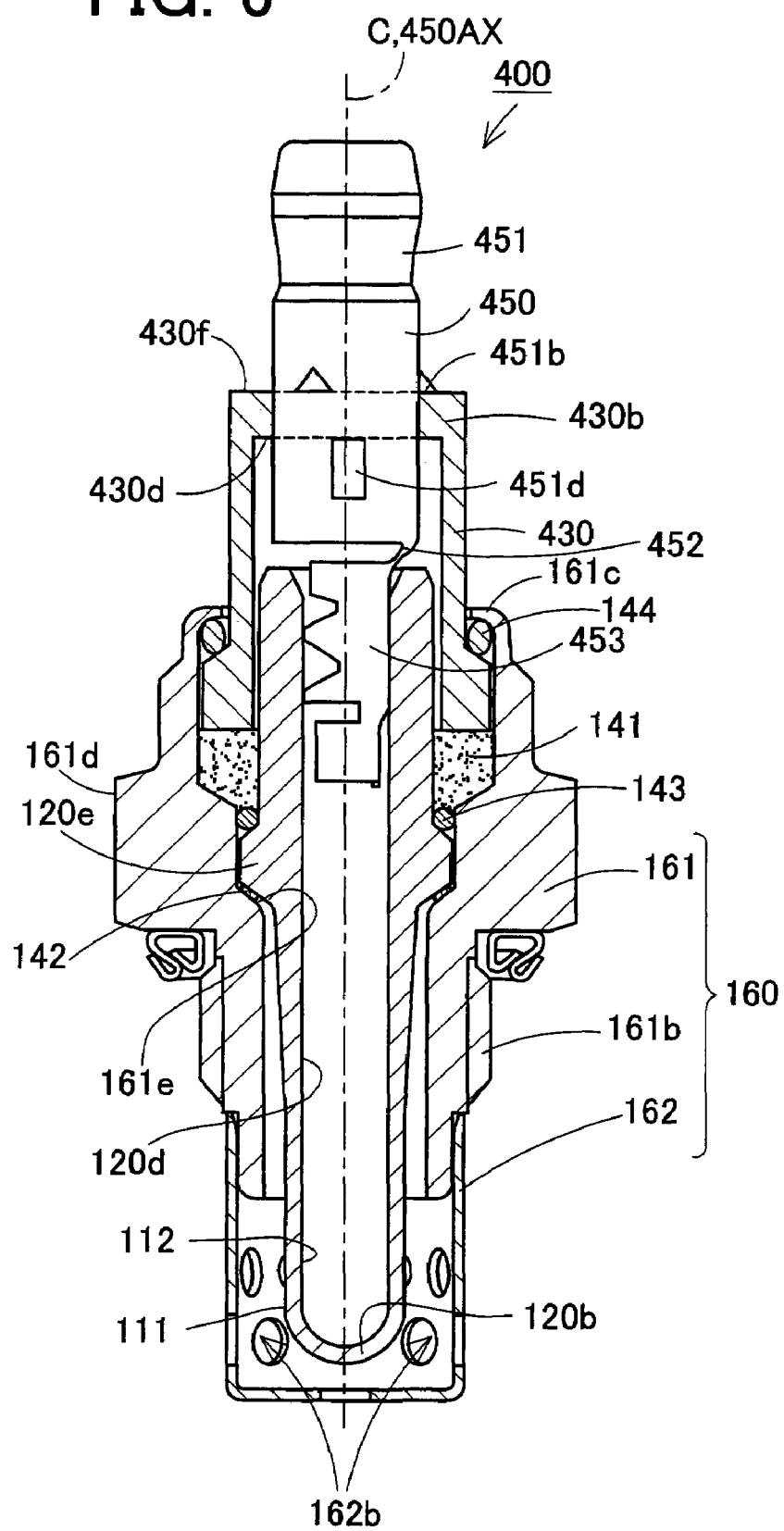
FIG. 6 is a partial sectional view of a gas sensor 400 in a second embodiment.

FIG. 6 is a partial sectional view of a gas sensor 400 in a second embodiment. The gas sensor 400 of the second embodiment is similar to the gas sensor 100 of the first embodiment, except for the shape of the terminal member and enclosure.

The gas sensor 400 comprises, same as the gas sensor 100 of the first embodiment, a gas detecting element 120, an outside electrode 111, an inside electrode 112, and a casing 160, and also an enclosure 430 and a terminal member 450 which are different from the gas sensor 100 in the first embodiment.

The enclosure 430 is made of insulating ceramics and formed in a cylindrical shape same as the enclosure 130 in the first embodiment, but the length in the axial direction is shorter than in the enclosure 130 in the first embodiment.

Figure 7:
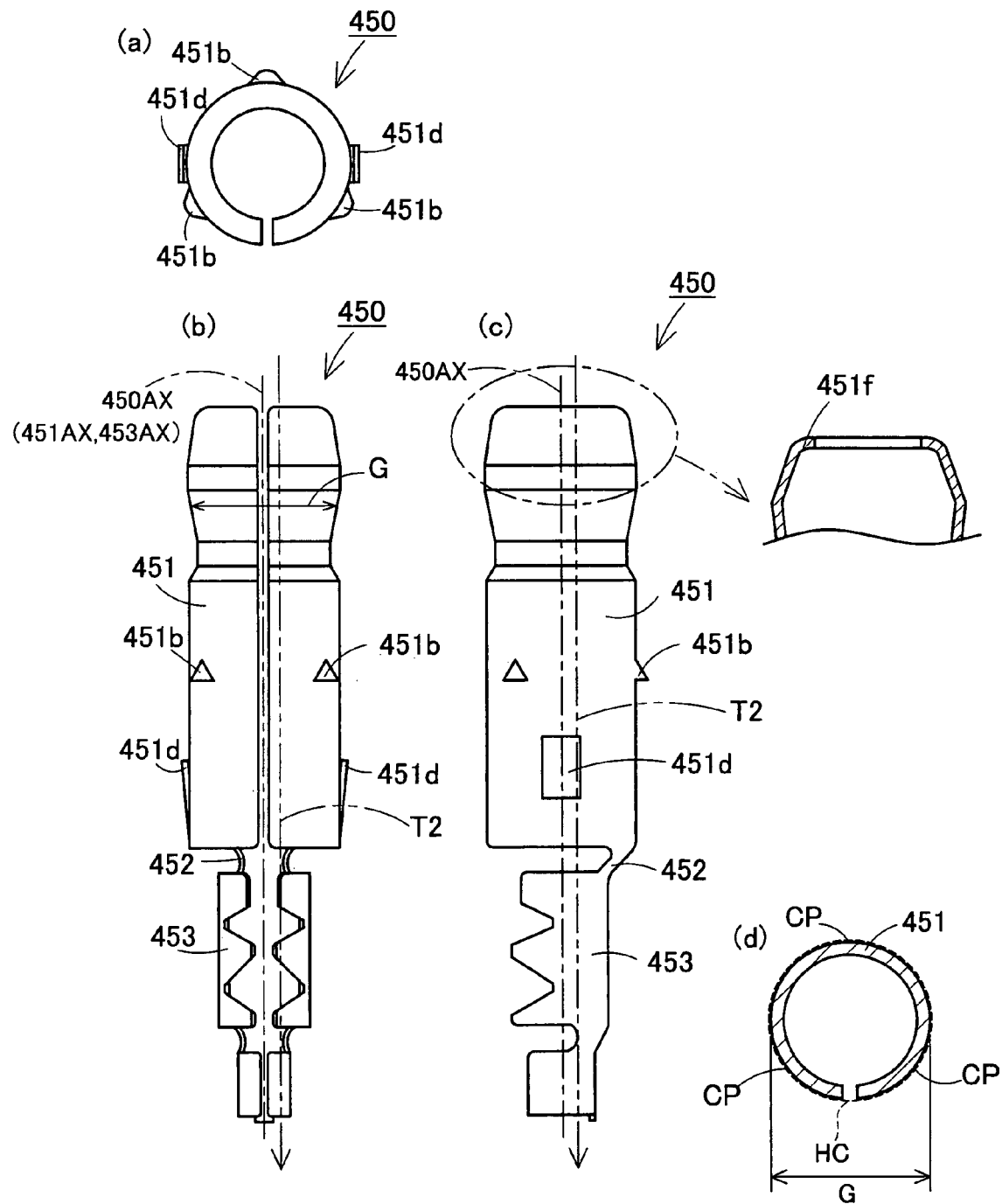
FIG. 7 is a diagram of a terminal member 450 in the second embodiment, in which (a) is a top view, (b) is a front view, (c) is a side view and a sectional view of a rear end 455, and (d) is an end view of cross section of an output-side terminal portion.

The terminal member 450 is a tubular form as shown in FIG. 7, having an output-side terminal portion 451, an element-side terminal portion 453, and a joint portion 452 for coupling the two.

The outtput-side terminal portion 451 is a tubular form with a C-shaped section (see FIG. 7 (d)) orthogonal to the axis line 451AX (axis line 450AX of the terminal member), and by moving the cap terminal 511 (see FIG. 8) of the cap terminal member 510 relatively in the direction (vertical direction in FIG. 6) along the axis line 450AX, when inserted and connected into the side of the cap terminal 511 (see FIG. 8) of the cap terminal member 510, it is designed to contract elastically in diameter.

At three positions in the peripheral direction of the middle of the axial direction, bumps 451b protruding to the radially outer side are formed. The bumps 451b abut against the rear end surface 430f of the enclosure 430, and prevent the output-side terminal portion 451 from invading into the enclosure 430 (see FIG. 6).

Furthermore, at the leading end of the output-side terminal portion 451, an outside bent portion 451d is formed by blanking and folding to the radially outer side. This outside bent portion 451d abuts against the leading end surface 430d of the step portion 430b of the enclosure 430, and prevents the output-side terminal portion 451 from slipping out (see FIG. 6).

The element-side terminal portion 453 is a tubular form with a C-shaped section orthogonal to the axis line 453AX (axis line 450AX of the terminal member). As shown in FIG. 6, the element-side terminal portion 453 is inserted into the gas detecting element 120 while contracting elastically in diameter, and is connected electrically to the inside electrode 112. Therefore, in the gas sensor 400, the element-side terminal portion 453 presses the inside electrode 112 from the inside toward the radially outer side to connect electrically. Hence, it lowers the risk of causing noise or the like due to momentary disconnection of the two by the effects of vibrations or the like.

Since the element-side terminal portion 453 contracts elastically in diameter, the element-side terminal portion 453 and the inside electrode 112 can be connected directly. Hence, as compared with the prior art of inserting an elastic conductive packing, this conductive packing can be omitted, and the number of parts is curtailed and the cost is lowered.

Such terminal member 450 can be integrally formed by pressing, by using a single metal plate of predetermined shape. It is hence easy to form and low in cost. A metal plate is bent and processed to form such terminal member 450, and the output-side terminal portion 451 and the element-side terminal portion 453 are formed in a tubular shape, and a ventilation passage T2 for introducing the reference gas (outer air) into the inside of the gas detecting element 120 is formed (see FIG. 7, FIG. 9). Hence, it does not require the process of forming the ventilation passage (for example, piercing process) after bending and processing the terminal member 450, and hence the cost is lower.

The terminal member 450 formed of a bent and processed plate material tends to be lower in rigidity as compared with one formed by processing a bar metal element. In particular, the output-side terminal portion 451 connecting to the cap terminal 511 is likely to be loaded by effects of external vibrations, and lowering of rigidity of the terminal member is not preferred. In the terminal member 450 of the present embodiment, by contrast, the rear end portion 451f of the output-side terminal portion 451 is bent to the radial inner side as shown in the partial sectional view in FIG. 7(c). Hence, the output-side terminal portion 451 can be elastically contracted in diameter, and the rigidity is enhanced.

As shown in FIG. 7(b), (d), of the output-side terminal portion 451, diameter G of a virtual cylinder (virtual circle) passing through contact points CP contacting with bumps 511b of the cap terminal 511 described below is supposed to be inside diameter of the output-side terminal portion 451.

Figure 8:
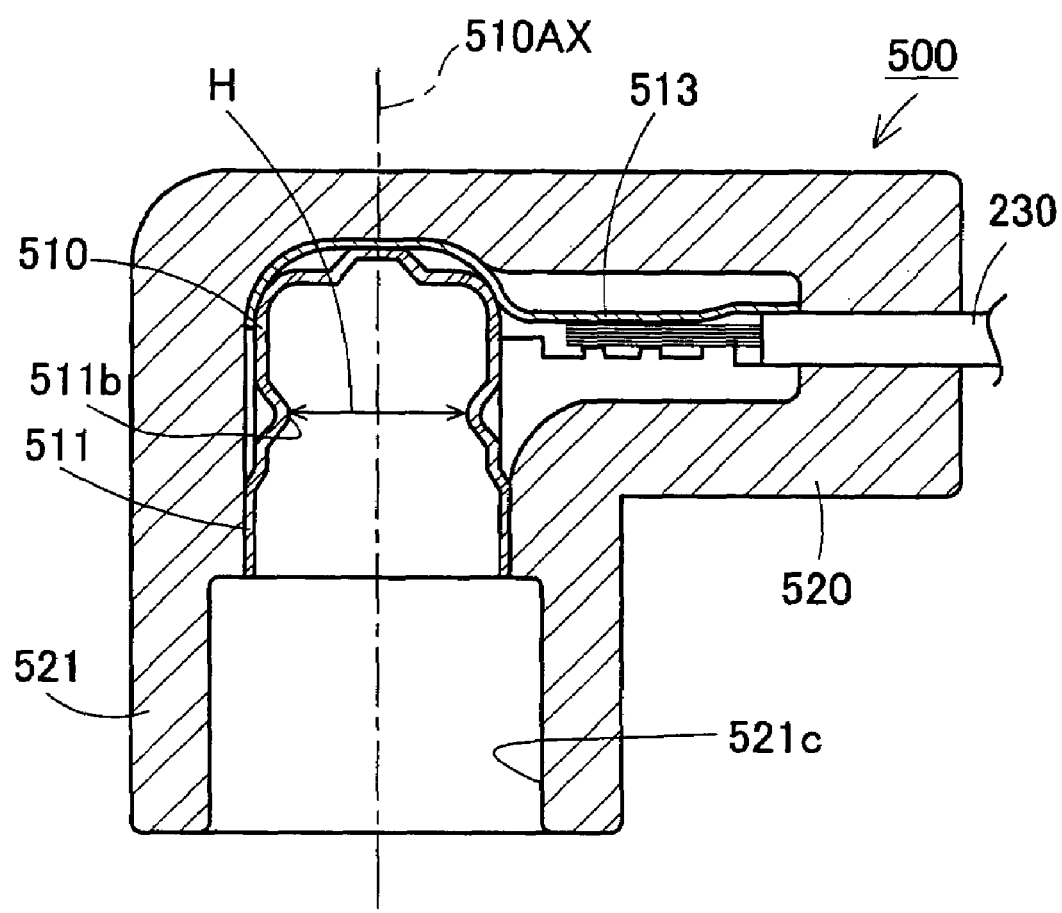
FIG. 8 is a partial sectional view of a gas sensor cap 500 in the second embodiment.

The gas sensor cap 500 of the second embodiment is explained by referring to the drawing. FIG. 8 is a partial sectional view of the gas sensor cap 500. The gas sensor cap 500 comprises a cap terminal member 510, a cover 520 for covering the cap terminal member 510, and a lead wire 230.

The cap terminal member 510 has a cylindrical cap terminal 511 with a bottom having a U-shaped section, and a tightening portion 513 for tightening and connecting the lead wire 230.

Next, the cap terminal 511 has enough rigidity for contracting the output-side terminal portion 451 in diameter without deforming itself when the output-side terminal portion 451 of the gas sensor 400 is inserted and connected in the inside. The cap terminal 511 has bumps 511*b* protruding to the radial inner side, formed at three positions in the peripheral direction in the middle of its axis line 510AX direction. Diameter H of a virtual circle contacting with the three bumps 511*b* is supposed to be inside diameter of the cap terminal 511 (see FIG. 8).

The lead wire 230 has its one end tightened to the tightening portion 513 of the cap terminal member 510, and is electrically connected to the cap terminal 511 same as in the first embodiment. Through this lead wire 230, the output signal from the gas detecting element 120 of the gas sensor 400 can be transmitted to an external device (for example, ECU).

The cover 520 is a hollow form made of fluorine rubber, having a cylindrical enclosure cover portion 521. An annular inside portion of the enclosure cover portion 521 is an contact portion 521*c*.

Figure 9:
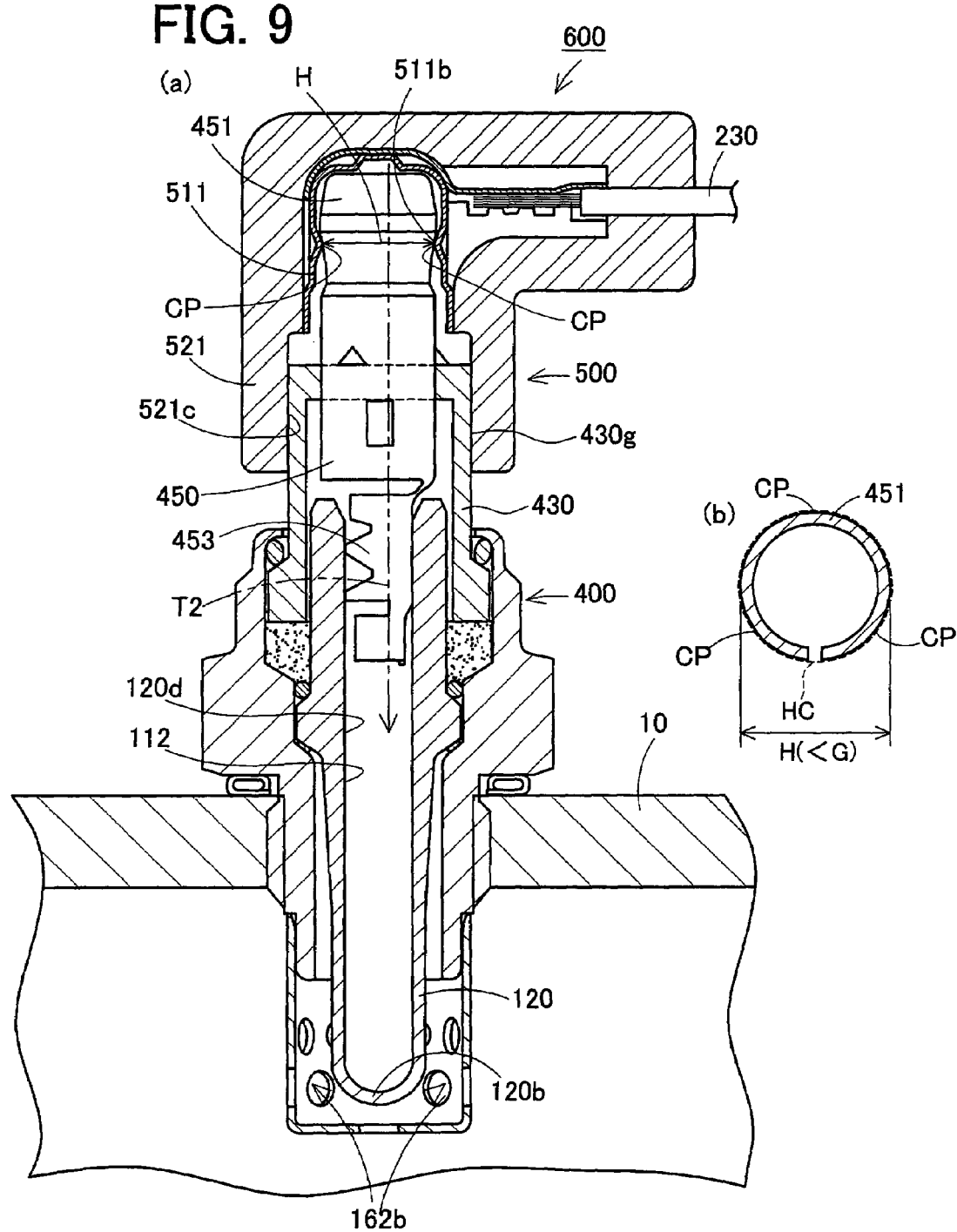
FIG. 9 (a) is an explanatory diagram of a gas sensor unit 600 in the second embodiment, showing a mode of its use, and (b) is an end view of cross section of an output-side terminal portion 451 of the terminal member 450.

FIG. 9 shows a mode of use of the gas sensor unit 600 composed of gas sensor 400 and gas sensor cap 500 in the second embodiment. This gas sensor unit 600 is used, for example, in detection of oxygen concentration in the emission of an internal-combustion engine, same as in the first embodiment.

More specifically, same as in the first embodiment, the gas sensor 400 is installed in the exhaust pipe 10. Next, in order that the output-side terminal portion 451 of the gas sensor 400 may be inserted into the cap terminal 511 of the gas sensor cap 500, the cap terminal 511 is moved in the direction (vertical direction in FIG. 8) along its axis line 510AX, and the gas sensor cap 500 is fitted on the gas sensor 400.

At this time, since the outside diameter G (see FIG. 7) of the output-side terminal portion 451 is greater than the inside diameter H (see FIG. 8) of the cap terminal 511 (G>H), the output-side terminal portion 451 receives a force toward the radial inner side from the bumps 511*b* of the cap terminal 511, and as shown in FIG. 9(*b*), the output-side terminal portion 451 contracts elastically so that the diameter of a virtual cylinder (virtual circle) HC at the section of the portion contacting with the bumps 511*b* of the output-side terminal portion 451 may be equal to H.

Therefore, the output-side terminal portion 451 is connected electrically while elastically pressing the bumps 511*b* of the cap terminal 511 to the radially outer side at plural (three in this embodiment) contact points CP by its own elasticity. Thus, in this second embodiment, also, the output-side terminal portion contacts with the cap terminal 511 at plural contact points CP. Since the contact points CP elastically press the cap terminal 511, it lowers the risk of causing noise or the like (the risk of lowering the gas detection accuracy) due to momentary disconnection between the output-side terminal portion 451 and cap terminal 511 by the effects of vibration of vehicle or the like. Since the gas sensor unit 600 is low in the risk of reduction of gas detection precision due to vibration effects, it can be favorably used in a two-wheel vehicle, in particular.

The output-side terminal portion 451 is elastically connected to the cap terminal 511 along the radial direction (lateral direction in FIG. 9) orthogonal to the axis line 451AX (see FIG. 7), and by moving the cap terminal 511 in the direction (vertical direction in FIG. 8) along the axis line 510AX of the cap terminal member 510, it can be easily detached from or attached to the output-side terminal portion 451, and the detaching and attaching property is improved.

Moreover, the output-side terminal portion 451 and cap terminal 411 contact with each other at contact points CP disposed on the virtual cylinder HC, and it is enough by putting the cap terminal 511 on the output-side terminal portion 451, with the axis line 451AX (see FIG. 7) of the output-side terminal portion 451 being coaxial with the axis line 510AX (see FIG. 8) of the cap terminal member 510. That is, to the output-side terminal portion 451 of the gas sensor 400 (see FIG. 9) installed in the exhaust pipe 10, the cap terminal 511 of the gas sensor cap 500 can be connected from any direction around its axis line C.

By fitting the gas sensor cap 500 to the gas sensor 400, the enclosure 430 can be covered by the enclosure cover portion 521 of the gas sensor cap 500. Hence, if pebbles or foreign matters are thrown toward the enclosure 430 while the vehicle is running, the portion of the enclosure 430 covered with the rubber enclosure cover portion 521 is protected from breakage.

Further, the annular contact portion 521*c* of the rubber enclosure cover 521 can be made tightly contact with the outer surface 430*g* of the enclosure 430 along the peripheral direction (360 degrees) thereof. Hence, invasion of water into the gas sensor unit 600 from the gap of the gas sensor 400 and gas sensor cap 500 can be prevented.

In such gas sensor unit 600, same as the gas sensor unit 300 in the first embodiment, reference gas (outer air) is introduced into the cover 520 from outside through the lead wire 230 of the gas sensor cap 500, and the reference gas can be taken into the inside (in the tube) of the gas detecting element 120 by way of the terminal member 450 (ventilation passage T2).

The invention is described herein by referring to embodiments 1 and 2 and modified example, but the invention is not limited to these embodiments alone, but may be changed and modified within the scope not departing from the true spirit and scope thereof.

For example, in the gas sensors 100, 400 in embodiments 1 and 2, a heater may be provided for heating the gas detecting element 120.

In the gas sensors 100, 400 in embodiments 1 and 2, the terminal members 150, 450 having output-side terminal portions 151, 451 and element-side terminal portions 153, 453 are formed integrally by using a single plate, but the output-side terminal portion and element-side terminal portion may be formed separately, and joined by welding or other method to form a terminal member.

In the gas sensors 100, 400 in embodiments 1 and 2, further, the output-side terminal portions 151, 451 and element-side terminal portions 153, 453 are formed in a tubular shape with a C-shaped section orthogonal to the axial direction. Not limited to such shape, however, a plate material may be wound into a tubular form by overlapping in part. The sectional shape orthogonal to the axial direction is not limited to C-shape, but may include circular or polygonal shape.

Figure 10:
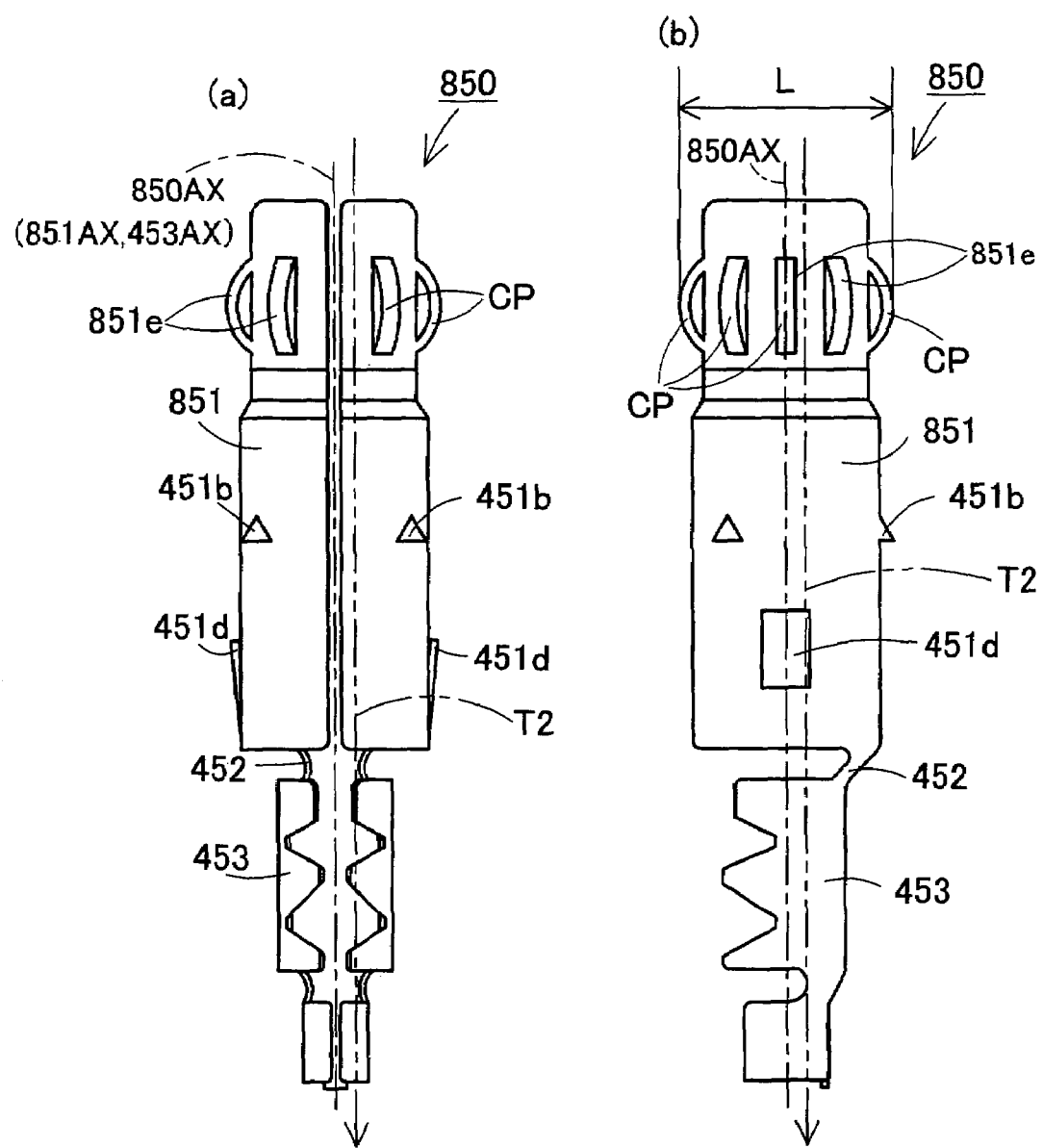
FIG. 10 is a diagram of a terminal member 850 in another embodiment, in which (a) is a front view, and (b) is a side view.

At the output-side terminal portion, the shape of the contact portion with the external terminal (cap terminal) is the bumps 151*b* in the first embodiment, and the inside bent tongue portions 751*b* in the modified example. In the second embodiment, the outer surface of the C-shaped section output-side terminal portion 451 is shown as the contact portion. Other modified examples may be also possible. For example, in the terminal member 850 shown in FIG. 10, the portion of the output-side terminal portion 851 enclosed by two slits extending in the direction along the axis line 851AX at the rear end is formed by protruding in an arc shape toward the radially outer side, and the slit protrusions 851*e* movable elastically in the radial direction are scattered and disposed at plural positions in the peripheral direction. In this output-side terminal portion 851, the peak of the slit protrusions 851e are the contact points CP with the external terminal (cap terminal), and the diameter L of the virtual cylinder passing these plural contact points CP becomes smaller elastically when connected to the external terminal, that is, it contracts in diameter.

INDUSTRIAL APPLICABILITY

The invention is applicable to a gas sensor having a gas detecting element, a gas sensor cap connected to the gas sensor for sending an output signal to an external device, and a gas sensor unit connecting the terminal member of the gas sensor and the gas sensor cap.

The invention claimed is:

1. A gas sensor comprising:
a gas detecting element, and
a terminal member connected to an electrode formed on the gas detecting element, the terminal member being connectable to an external terminal for sending an output signal from the gas detecting element to outside,
wherein the terminal member includes:
an output-side terminal portion engageable and electrically connectable with the external terminal for sending the output signal,
the output-side terminal portion having a plurality of contact points at which the output-side terminal portion elastically contacts with the external terminal to hold the external terminal in a direction orthogonal to a moving direction that moves at least either the external terminal or the output-side terminal portion relatively when the terminal member is connected with the external terminal, and
an element-side terminal portion electrically connected to the electrode, wherein the gas detecting element is composed of ceramics, having a tubular form with a bottom closed at a leading end side in an axial direction of the gas detecting element,
the electrode is an inside electrode formed on an inner surface of the gas detecting element,
the terminal member is made of a plate material bent and formed in a predetermined shape,
the output-side terminal portion is tubular, and is elastically expanded or contracted in diameter when connected to the external terminal, and
the element-side terminal portion is tubular, and inserted as being elastically contracted in diameter in the gas detecting element, the element-side terminal portion being electrically connected to the inside electrode.

2. The gas sensor as set forth in claim 1,
wherein the plurality of contact points of the output-side terminal portion is disposed on a virtual cylinder passing them, and
the contact points move so as to expand or contract a diameter of the virtual cylinder when the output-side terminal portion is connected to the external terminal.

3. The gas sensor as set forth in claim 1,
wherein the output-side terminal portion is elastically contracted in diameter when inserted in the external terminal and connected thereto, and
the output-side terminal portion has a rear end portion inwardly bent and positioned at a rear end side in the axial direction.

4. The gas sensor as set forth in claim 1,
wherein the terminal member is made of a single plate material formed integrally.

5. The gas sensor as set forth in claim 1,
wherein the output-side terminal portion of the terminal member has a C-shape in section orthogonal to an axis thereof.

6. A gas sensor unit comprising:
a gas sensor including a gas detecting element and a terminal member that is connected to an electrode formed in the gas detecting element and also is connected to an external terminal for sending an output signal from the gas detecting element to outside, and
a gas sensor cap having a cap terminal serving as the external terminal connected to the terminal member of the gas sensor for transmitting the output signal to an external device,
wherein the terminal member includes:
an output-side terminal portion engaged and connected electrically with the cap terminal to send the output signal,
the output-side terminal portion having a plurality of contact points at which the output-side terminal portion is elastically connected with the cap terminal along a direction orthogonal to a moving direction for relatively moving either the cap terminal or the output-side terminal portion when connected to the cap terminal,
the output-side terminal portion of the terminal member is tubular, and is elastically expanded or contracted in diameter when connected to the cap terminal, and
the cap terminal is tubular, and is engaged with the output-side terminal portion by expanding or contracting the output-side terminal portion in diameter without deforming itself.

7. The gas sensor unit as set forth in claim 6,
wherein the plurality of contact points of the output-side terminal portion of the terminal member is disposed on a virtual cylinder passing them, and the contact points move so as to expand or contract a diameter of the virtual cylinder when the output-side terminal portion is connected to the cap terminal.

8. The gas sensor unit as set forth in claim 6,
wherein the gas detecting element is composed of ceramics, and has a tubular shape with a bottom closed at the leading end side in an axial direction of the gas detecting element, and
the electrode is an inside electrode formed on the inner surface of the gas detecting element, and
the terminal member is made of a plate material bent and formed in a predetermined shape and has a tubular element-side terminal portion inserted as being elastically contracted in diameter in the gas detecting element, the element-side terminal portion being electrically connected to the inside electrode.

9. The gas sensor unit as set forth in claim 8,
wherein the gas sensor cap has an inside space communicating with outside, and
inside of the gas detecting element and the inside space of the gas sensor cap are in communication with each other through inside of the output-side terminal portion and inside of the element-side terminal portion of the terminal member.

10. The gas sensor unit as set forth in claim 8,
wherein the terminal member is made of a single plate material formed integrally.

11. The gas sensor unit as set forth in claim 6,
wherein the output-side terminal portion of the terminal member of the gas sensor has a C-shape in section orthogonal to its axis.

12. The gas sensor unit as set forth in claim 6,
wherein the gas sensor has a tubular enclosure made of insulating ceramics and placed to surround the gas detecting element and terminal member,
the gas sensor cap has a cover made of insulating rubber and formed to cover the cap terminal, and
this cover includes an enclosure cover portion covering at least part of the tubular enclosure of the gas sensor connected with the gas sensor cap.

13. The gas sensor unit as set forth in claim 12,
wherein the enclosure cover portion of the gas sensor cap has an annular close-contact portion held circumferentially in close contact with an outer surface of the tubular enclosure, and
the close-contact portion is in contact with an outer surface of a rear end portion of the tubular enclosure positioned at a rear end side in the axial direction thereof when the gas sensor cap is connected to the gas sensor.

14. A gas sensor comprising:
a gas detecting element, and
a terminal member connected to an electrode formed on the gas detecting element, the terminal member being connectable to an external terminal for sending an output signal from the gas detecting element to outside,
wherein the terminal member includes:
an output-side terminal portion engageable and electrically connectable with the external terminal for sending the output signal,
the output-side terminal portion having a plurality of contact points at which the output-side terminal portion elastically contacts with the external terminal to hold the external terminal in a direction orthogonal to a moving direction that moves at least either the external terminal or the output-side terminal portion relatively when the terminal member is connected with the external terminal, and
an element-side terminal portion electrically connected to the electrode,
wherein the gas detecting element is composed of ceramics, having a tubular form with a bottom closed at a leading end side in an axial direction of the gas detecting element,
the electrode is an inside electrode formed on an inner surface of the gas detecting element,
the gas sensor further comprises a tubular enclosure made of insulating ceramics and surrounding the gas detecting element and the terminal member,
the terminal member is made of a plate material bent and formed in a predetermined shape,
the output-side terminal portion is tubular, and is elastically expanded in diameter when the external terminal is inserted in the output-side terminal portion for connection, thereby reducing a gap between an outer surface of the output-side terminal portion and an inner surface of the tubular enclosure than before insertion, and
the element-side terminal portion is tubular, and inserted as being elastically contracted in diameter in the gas detecting element, the element-side terminal portion being electrically connected to the inside electrode.

15. A gas sensor unit comprising:
a gas sensor including a gas detecting element and a terminal member that is connected to an electrode formed in the gas detecting element and also is connected to an external terminal for sending an output signal from the gas detecting element to outside, and
a gas sensor cap having a cap terminal serving as the external terminal connected to the terminal member of the gas sensor for transmitting the output signal to an external device,
wherein the terminal member includes:
an output-side terminal portion engaged and connected electrically with the cap terminal to send the output signal,
the output-side terminal portion having a plurality of contact points at which the output-side terminal portion is elastically connected with the cap terminal along a direction orthogonal to a moving direction for relatively moving either the cap terminal or the output-side terminal portion when connected to the cap terminal,
wherein the gas sensor has a tubular enclosure made of insulating ceramics and surrounding the gas detecting element and the terminal member,
the output-side terminal portion of the terminal member is tubular, and is elastically expanded in diameter when the cap terminal is inserted in of the output-side terminal portion, and
the cap terminal has enough rigidity to expand the output-side terminal portion in diameter without deforming itself when inserted in and connected with the inside of the output-side terminal portion, and
the cap terminal is inserted in and connected with an inside of the output-side terminal portion, the output-side terminal portion being elastically expanded in diameter, providing a smaller gap than before insertion between an outer surface of the output-side terminal portion and an inner surface of the tubular enclosure.

16. A gas sensor unit comprising:
a gas sensor including a gas detecting element and a terminal member that is connected to an electrode formed in the gas detecting element and also is connected to an external terminal for sending an output signal from the gas detecting element to outside, and
a gas sensor cap having a cap terminal serving as the external terminal connected to the terminal member of the gas sensor for transmitting the output signal to an external device,
wherein the terminal member includes:
an output-side terminal portion engaged and connected electrically with the cap terminal to send the output signal,
the output-side terminal portion having a plurality of contact points at which the output-side terminal portion is elastically connected with the cap terminal along a direction orthogonal to a moving direction for relatively moving either the cap terminal or the output-side terminal portion when connected to the cap terminal,
wherein the gas sensor has a tubular enclosure made of insulating ceramics and placed to surround the gas detecting element and terminal member,
the gas sensor cap has a cover made of insulating rubber and formed to cover the cap terminal, and
this cover includes an enclosure cover portion covering at least part of the tubular enclosure of the gas sensor connected with the gas sensor cap, and
wherein the enclosure cover portion of the gas sensor cap has an annular close-contact portion held circumferentially in close contact with an outer surface of the tubular enclosure, and
the close-contact portion is in contact with an outer surface of a rear end portion of the tubular enclosure positioned at a rear end side in the axial direction thereof when the gas sensor cap is connected to the gas sensor.

* * * * *